United States Patent
Edwards et al.

(12) 
(10) Patent No.: US 6,524,554 B1
(45) Date of Patent: Feb. 25, 2003

(54) RADIOPHARMACEUTICALS FOR IMAGING INFECTION AND INFLAMMATION AND FOR IMAGING AND TREATMENT OF CANCER

(75) Inventors: David Scott Edwards, Burlington, MA (US); Milind Rajopadhye, Westford, MA (US)

(73) Assignee: Bristol-Myers Squibb Pharma Company, Princeton, NJ (US)

(*) Notice: Subject to any disclaimer, the term of this patent is extended or adjusted under 35 U.S.C. 154(b) by 0 days.

(21) Appl. No.: 09/285,280

(22) Filed: Apr. 2, 1999

Related U.S. Application Data

(60) Provisional application No. 60/080,672, filed on Apr. 3, 1998.

(51) Int. Cl.$^7$ ............................................. A61K 49/04
(52) U.S. Cl. ..................... 424/9.4; 424/1.11; 424/1.65; 424/1.69; 424/9.1; 534/10; 534/14
(58) Field of Search ................. 534/7, 10–16; 424/1.11, 1.65, 1.69, 9.1, 9.4, 9.5, 9.6, 9.7, 9.8; 206/223, 569, 570

(56) References Cited

U.S. PATENT DOCUMENTS

| | | |
|---|---|---|
| 4,988,827 A | 1/1991 | Bergstein et al. |
| 5,350,837 A | 9/1994 | Bridger et al. |
| 5,376,356 A | 12/1994 | Morgan, Jr. |
| 5,480,970 A | 1/1996 | Pollak et al. |
| 5,569,745 A | 10/1996 | Goodbody et al. |
| 5,659,041 A | 8/1997 | Pollak et al. |
| 5,662,885 A | 9/1997 | Pollak et al. |
| 5,679,642 A | 10/1997 | Goodbody et al. |

FOREIGN PATENT DOCUMENTS

| | | | |
|---|---|---|---|
| WO | 9522996 | * | 8/1995 |
| WO | 9631243 | * | 10/1996 |
| WO | 9640637 | * | 12/1996 |
| WO | 9815295 | * | 4/1998 |
| WO | 9853858 | * | 12/1998 |

OTHER PUBLICATIONS

Edwards et al: "New and Versatile Ternary Ligand System for Technetium Radiopharmaceuticals: Water Soluble Phosphines and Tricine as Coligands in Labeling with Hydrazinonicotinamide–modified Cyclic Glycoprotein IIB/IIIA Receptor Anatagonist with 99MTC" Bioconjugate Chemistry, vol. 8, No. 2, Mar. 1, 1997, pp. 146–154.*
Fischman et. al., Semin. Nucl. Med., 1994, 24, pp 154–168.
Merrified, J. Am. Chem. Soc., 85, 2149–2154 (1963).
(DeGrado and Kaiser (1980) *J. Org. Chem.* 45, 1295–1300).
Cheung et al., (1977) *Can. J. Chem.* 55, pp. 906–910.
Freidinger et al., (1982) *J. Org. Chem.* 48, 77 (1982).
Brinkley, M., *Bioconjugate Chemistry* 1992, 3(1).

* cited by examiner

*Primary Examiner*—Dameron L. Jones
(74) *Attorney, Agent, or Firm*—Paul D. Golian

(57) ABSTRACT

The present invention provides novel radiopharmaceuticals comprising one to three pentapeptides, $X^1X^2X^3X^4X^5$, independently attached to a metal chelator or bonding moiety, $C_h$, to which is attached a Tc-99m, Re-186, or Re-188, optionally further comprising a linking group, $L_n$, between the peptides and the chelator or bonding moiety. The pentapeptide sequence binds to the tuftsin receptor and is attached at the N-terminus to $L_n$ or $C_h$. These radiopharmaceuticals are useful for the diagnosis of infection and inflammation, reagents and kits useful for preparing the radiopharmaceuticals, methods of imaging sites of infection and/or inflammation in a patient, and methods of diagnosing diseases associated with infection or inflammation in patients in need of such diagnosis.

22 Claims, No Drawings

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: artificial sequence
<220> FEATURE:
<221> NAME/KEY: VARIANT
<222> LOCATION: (1)..(1)
<223> OTHER INFORMATION: Xaa is Thr, Ser, 3Hyp, or 4Hyp
<220> FEATURE:
<221> NAME/KEY: VARIANT
<222> LOCATION: (2)..(2)
<223> OTHER INFORMATION: Xaa is Lys, Orn, Arg, 2-aminoethycysteine, or
      Gln
<220> FEATURE:
<221> NAME/KEY: VARIANT
<222> LOCATION: (3)..(4)
<223> OTHER INFORMATION: Xaa is Pro or homoproline
<220> FEATURE:
<221> NAME/KEY: VARIANT
<222> LOCATION: (5)..(5)
<223> OTHER INFORMATION: Xaa is Lys, Orn, Arg, Gln, or
      2-amino-5-(2-imidazolin-2-ylamino) pentanoic acid

<400> SEQUENCE: 1

Xaa Xaa Xaa Xaa Xaa
1               5
```

RADIOPHARMACEUTICALS FOR IMAGING INFECTION AND INFLAMMATION AND FOR IMAGING AND TREATMENT OF CANCER

This application claims the benefit of U.S. Provisional Application No. 60/080,672, filed Apr. 3, 1998.

FIELD OF THE INVENTION

The present invention provides novel radiopharmaceuticals useful for the diagnosis of infection, inflammation, and cancer, reagents and kits useful for preparing the radiopharmaceuticals, methods of imaging sites of infection and/or inflammation, and cancer in a patient, and methods of diagnosing cancer and diseases associated with infection or inflammation in patients in need of such diagnosis. The present invention also provides novel readiopharmaceuticals for treating cancer. The radiopharmaceuticals bind in vivo to the tuftsin receptor on the surface of neutrophils and monocytes which accumulate at the site of infection, inflammation, and in tumors.

BACKGROUND OF THE INVENTION

The rapid diagnosis of diseases associated with focal infection and inflammation is a currently unmet clinical need. Inflammation is the result of the detection of an abnormality in the body, such as infection, or a tumor, by white blood cells, including neutrophils and monocytes. White cells become activated and gravitate toward the site of the abnormality. When the white cells become fully activated they degranulate and release proteolytic enzymes as well as chemoattractants resulting in a chemotactic gradient and as a consequence the recruitment of additional white cells. The result is a concentration of activated white cells at the site. This localization provides a means for diagnosing diseases associated with infection and inflammation and cancer through the use of white cells labeled with an externally detectable radioisotope and gamma scintigraphy.

Two approaches have been taken to utilize this mechanism for imaging infection and inflammation. The first involves isolating white cells from a patient, labeling the white cells with a radioisotope and then reinjecting the radiolabeled autologous white cells into the patient. This approach has several drawbacks including the effect of the labeling methodology on the biological activity of the white cells manifest as a diminished number of competent white cells, and the hazards and inconvenience of handling the patient's blood. The second approach involves injecting into the patient a radiopharmaceutical that binds to activated white cells in vivo.

An example of the in vivo labeling approach is the use of radiolabeled monoclonal antibodies or fragments thereof that are directed against a white cell activation marker, as described in Morgan, Jr., U.S. Pat. No. 5,376,356. A white cell activation marker is an antigen on the surface of the white cell that is poorly expressed or not expressed at all until activation of the white cell. This approach suffers from the disadvantages associated wit h the use of many proteinaceous radiopharmaceuticals as diagnostics, namely, generally slow blood clearance which results in high background activity unless an inconveniently long period of time is allowed to pass between injection and imaging, and the possibility of an allergic reaction by the patient to a foreign protein.

It has been proposed that these problems can be overcome by using radiolabeled peptides that bind in vivo to surface receptors on activated white cells (Fischman et. al., Semin. Nucl. Med., 1994, 24, pp 154–168). The chemotactic peptide, fMLF, labeled with In111 or Tc-99m have been shown to accumulate at sites of infection in experimental animal models. However, the peptide fMLF is a potent agonist for the white cells and thus has limited clinical applicability in a diagnostic radiopharmaceutical. The limitations include the potential for serious deleterious effects to the patient, such as a severe drop in white blood cell count, resulting from the activation of the white cells upon injection of even small amounts of the potent agonist peptide.

An alternative approach based on the use of radiolabeled tuftsin receptor antagonists has been disclosed by Pollak, A., U.S. Pat. Nos. 5,480,970, 5,659,041, 5,662,885, and Goodbody, A., U.S. Pat. Nos. 5,569,745, and 5,679,642. These patents disclose the use of Tc-99m chelate conjugates of the tuftsin receptor antagonist Thr-Lys-Pro-Pro-Arg for imaging infection and inflammation. The chelators are diamidedithiols ($N_2S_2$) and triamidethiols ($N_3S$). The chelator may optionally be attached to the tuftsin antagonist via a linking group. The chelators disclosed do not generally form Tc-99m complexes with high labeling efficiency; that is moderate-to-high concentrations of the antagonist-chelator conjugates are required to obtain high yields of the Tc-99m complexes under clinically practical conditions.

Co-pending U.S. Ser. No. 08/415,908, and U.S. Ser. No. 08/808,699, describe ternary ligand complexes of Tc-99m comprised of hydrazine modified peptides and two ancillary ligands. The peptides described bind to a variety of antigens including the GPIIb/IIIa receptor on activated platelets and the chemotactic peptide receptor on white cells. The Tc-99m complexes comprised of GPIIb/IIIa receptor antagonists are useful for imaging platelet deposition, such as thrombosis, and the Tc-99m complexes comprised of chemotactic peptide receptor agonists and antagonists are useful for imaging infection and inflammation. Co-pending U.S. Ser. No. 08/476,296 describes the stable hydrazone modified peptides as reagents for synthesizing these ternary ligand Tc-99m complexes.

It is the object of the present invention to provide novel radiopharmaceuticals for imaging infection and inflammation comprised of tuftsin receptor antagonists linked to hydrazine or stable hydrazone bonding units for Tc-99m. This invention also provides a novel means of imaging tumors using these radiopharmaceuticals. This invention further provides a novel means of treating tumors in a patient by administering radiopharmaceuticals of the present invention comprised of a beta-emitting isotope of rhenium.

SUMMARY OF THE INVENTION

The present invention provides novel radiopharmaceuticals useful for the diagnosis of infection and inflammation, reagents and kits useful for preparing the radiopharmaceuticals, methods of imaging sites of infection and/or inflammation in a patient, and methods of diagnosing diseases associated with infection or inflammation in patients in need of such diagnosis.

The radiopharmaceuticals bind in vivo to the tuftsin receptor on the surface of white cells which accumulate at the site of infection and inflammation.

The radiopharmaceuticals of the present invention are comprised of one to three pentapeptides, $X^1X^2X^3X^4X^5$, independently attached to a metal chelator or bonding moiety, $C_h$, to which is attached a Tc-99m, Re-186, or Re-188, optionally further comprising a linking group, $L_n$, between the peptides and the chelator or bonding moiety.

The peptides are comprised of a pentapeptide sequence that binds to the tuftsin receptor attached at the N-terminus to $L_n$ or $C_h$. The interaction of the pentapeptide recognition sequences of the radiopharmaceuticals with the tuftsin receptor on white blood cells results in localization of the radiopharmaceuticals in sites of infection and inflammation, and in tumors.

DETAILED DESCRIPTION OF THE INVENTION

[1] Thus, in a first embodiment, the present invention provides a novel compound capable of direct transformation into a radiopharmaceutical, the compound having the formula:

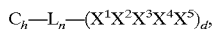

$$C_h-L_n-(X^1X^2X^3X^4X^5)_d,$$

wherein:

$X^1$ is an amino acid independently selected from the group: threonine, serine, 3-hydroxyproline, and 4-hydroxyproline;

$X^2$ is an amino acid independently selected from the group: lysine, ornithine, arginine, 2-aminoethylcysteine, and glutamine;

$X^3$ and $X^4$ are amino acids independently selected at each occurrence from the group: proline, and homoproline;

$X^5$ is an amino acid independently selected from the group: lysine, ornithine, arginine, glutamine, and 2-amino-5-(2-imidazolin-2-ylamino)pentanoic acid;

d is selected from 1, 2, and 3;

$L_n$ is a linking group having the formula:

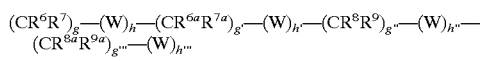

$$(CR^6R^7)_g-(W)_{h'}-(CR^{6a}R^{7a})_{g'}-(W)_{h''}-(CR^8R^9)_{g''}-(W)_{h'''}-(CR^{8a}R^{9a})_{g'''}-(W)_{h''''}$$

W is independently selected at each occurrence from the group: O, NH, NHC(=O), C(=O)NH, C(=O), C(=O)O, OC(=O);

$R^6$, $R^{6a}$, $R^7$, $R^{7a}$, $R^8$, $R^{8a}$, $R^9$ and $R^{9a}$ are independently selected at each occurrence from the group: =O, COOH, SO$_3$H, PO$_3$H, $C_1$–$C_5$ alkyl substituted with 0–3 $R^{10}$, aryl substituted with 0–3 $R^{10}$, benzyl substituted with 0–3 $R^{10}$, and $C_1$–$C_5$ alkoxy substituted with 0–3 $R^{10}$, NHC(=O)$R^{11}$, C(=O)NHR$^{11}$, NHC(=O) NHR$^{11}$, NHR$^{11}$, R$^{11}$, and a bond to $C_h$;

$R^{10}$ is independently selected at each occurrence from the group: a bond to $C_h$, COOR$^{11}$, OH, NHR$^{11}$, SO$_3$H, PO$_3$H, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$, and a bond to $C_h$;

$R^{12}$ is a bond to $C_h$;

h is selected from 0, 1, 2, 3, 4, and 5;

h' is selected from 0, 1, 2, 3, 4, and 5;

h" is selected from 0, 1, 2, 3, 4, and 5;

h'" is selected from 0, 1, 2, 3, 4, and 5;

g is selected from 0, 1, 2, 3, 4, 5, 6, 7, 8, 9, and 10;

g' is selected from 0, 1, 2, 3, 4, 5, 6, 7, 8, 9, and 10;

g" is selected from 0, 1, 2, 3, 4, 5, 6, 7, 8, 9, and 10;

g'" is selected from 0, 1, 2, 3, 4, 5, 6, 7, 8, 9, and 10;

$C_h$ is a metal bonding unit having the formula:

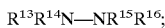

$$R^{13}R^{14}N-NR^{15}R^{16};$$

wherein:

$R^{13}$, and $R^{14}$ are each independently selected from the group: hydrogen, aryl substituted with 0–3 $R^{17}$, and a 5–10 membered heterocyclic ring system containing 1–4 heteroatoms independently selected from N, S, and O and substituted with 0–3 $R^{17}$;

$R^{15}$ and $R^{16}$ are both H, or combine to form =C(R$^{20}$)(R$^{21}$);

$R^{17}$ is independently selected at each occurrence from the group: a bond to $L_n$, F, Cl, Br, I, —CF$_3$, —CN, —CO$_2$R$^{18}$, —C(=O)R$^{18}$, —C(=O)N(R$^{18}$)$_2$, —CH$_2$OR$^{18}$, —OC(=O)R$^{18}$, —OC(=O)OR$^{18}$, —OR$^{18}$, —SO$_2$N(R$^{18}$)$_2$, $C_1$–$C_5$ alkyl, aryl substituted with 0–2 $R^{18}$, and a 5–10 membered heterocyclic ring system containing 1–4 heteroatoms independently selected from N, S, and O;

$R^{18}$ is independently selected at each occurrence from the group: a bond to $L_n$, H, $C_1$–$C_6$ alkyl, phenyl, and benzyl;

$R^{20}$ and $R^{21}$ are independently selected from the group: H, $C_1$–$C_{10}$ alkyl, —CN, —CO$_2$R$^{25}$, —C(=O)R$^{25}$, —C(=O)N(R$^{25}$)$_2$, $C_2$–$C_{10}$ 1-alkene substituted with 0–3 $R^{23}$, $C_2$–$C_{10}$ 1-alkyne substituted with 0–3 $R^{23}$, aryl substituted with 0–3 $R^{23}$, unsaturated 5–10 membered heterocyclic ring system containing 1–4 heteroatoms independently selected from N, S, and O and substituted substituted with 0–3 $R^{23}$, and unsaturated $C_{3-10}$ carbocycle substituted with 0–3 $R^{23}$;

alternatively, $R^{20}$ and $R^{21}$, taken together with the divalent carbon radical to which they are attached form:

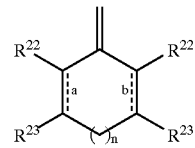

$R^{22}$ and $R^{23}$ are independently selected from the group: H, $R^{24}$, $C_1$–$C_{10}$ alkyl substituted with 0–3 $R^{24}$, $C_2$–$C_{10}$ alkenyl substituted with 0–3 $R^{24}$, $C_2$–$C_{10}$ alkynyl substituted with 0–3 $R^{24}$, aryl substituted with 0–3 $R^{24}$, a 5–10 membered heterocyclic ring system containing 1–4 heteroatoms independently selected from N, S, and O and substituted with 0–3 $R^{24}$, and $C_{3-10}$ carbocycle substituted with 0–3 $R^{24}$;

alternatively, $R^{22}$, $R^{23}$ taken together form a fused aromatic or a 5–10 membered heterocyclic ring system containing 1–4 heteroatoms independently selected from N, S, and O;

a and b indicate the positions of optional double bonds and n is 0 or 1;

$R^{24}$ is independently selected at each occurrence from the group: =O, F, Cl, Br, I, —CF$_3$, —CN, —CO$_2$R$^{25}$, —C(=O)R$^{25}$, —C(=O)N(R$^{25}$)$_2$, —N(R$^{25}$)$_3^+$, —CH$_2$OR$^{25}$, —OC(=O)R$^{25}$, —OC(=O)OR$^{25a}$, —OR$^{25}$, —OC(=O)N(R$^{25}$)$_2$, —NR$^{26}$C(=O)R$^{25}$, —NR$^{26}$C(=O)OR$^{25a}$, —NR$^{26}$C(=O)N(R$^{25}$)$_2$, —NR$^{26}$SO$_2$N(R$^{25}$)$_2$, —NR$^{26}$SO$_2$R$^{25a}$, —SO$_3$H, —SO$_2$R$^{25a}$, —SR$^{25}$, —S(=O)R$^{25a}$, —SO$_2$N(R$^{25}$)$_2$, —N(R$^{25}$)$_2$, =NOR$^{25}$, —C(=O)NHOR$^{25}$, —OCH$_2$CO$_2$H, and 2-(1-morpholino)ethoxy; and, R$^{25}$, R$^{25a}$, and R$^{26}$ are each independently selected at each occurrence from the group: hydrogen and C$_1$–C$_6$ alkyl;

and a pharmaceutically acceptable salt thereof.

[2] In a preferred embodiment, the present invention provides a compound, wherein:

X$^1$ is an amino acid independently selected from the group: threonine, and serine;

X$^2$ is an amino acid independently selected from the group: lysine, and ornithine;

X$^5$ is an amino acid independently selected from the group: lysine, 2-amino-5-(2-imidazolin-2-ylamino) pentanoic acid, and arginine;

W is independently selected at each occurrence from the group: O, NH, NHC(=O), C(=O)NH, and C(=O);

R$^6$, R$^{6a}$, R$^7$, R$^{7a}$, R$^8$, R$^{8a}$, R$^9$ and R$^{9a}$ are independently selected at each occurrence from the group: =O, COOH, SO$_3$H, PO$_3$H, C$_1$–C$_5$ alkyl substituted with 0–1 R$^{10}$, aryl substituted with 0–1 R$^{10}$, benzyl substituted with 0–1 R$^{10}$, and C$_1$–C$_5$ alkoxy substituted with 0–1 R$^{10}$, NHC(=O)R$^{11}$, C(=O)NHR$^{11}$, NHC(=O)NHR$^{11}$, NHR$^{11}$, R$^{11}$, and a bond to C$_h$;

R$^{10}$ is independently selected at each occurrence from the group: a bond to C$_h$, COOR$^{11}$, OH, NHR$^{11}$, SO$_3$H, aryl substituted with 0–1 R$^{11}$, C$_{1-5}$ alkyl substituted with 0–1 R$^{12}$, C$_{1-5}$ alkoxy substituted with 0–1 R$^{12}$, and a 5–10 membered heterocyclic ring system containing 1–4 heteroatoms independently selected from N, S, and O and substituted with 0–3 R$^{11}$;

R$^{11}$ is independently selected at each occurrence from the group: H, aryl substituted with 0–1 R$^{12}$, a 5–10 membered heterocyclic ring system containing 1–4 heteroatoms independently selected from N, S, and O and substituted with 0–1 R$^{12}$ and a bond to C$_h$;

h is 0 or 1;

h' is 0 or 1;

C$_h$ is a metal bonding unit having the formula:

R$^{13}$R$^{14}$N—NR$^{15}$R$^{16}$;

wherein:

R$^{17}$ is independently selected at each occurrence from the group: a bond to L$_n$, F, Cl, Br, I, —CF$_3$, —CN, —CO$_2$R$^{18}$, —C(=O)R$^{18}$, —C(=O)N(R$^{18}$)$_2$, —CH$_2$OR$^{18}$, —OC(=O)R$^{18}$, —OC(=O)OR$^{18}$, —OR$^{18}$, and —SO$_2$N(R$^{18}$)$_2$;

R$^{18}$ is independently selected at each occurrence from the group: a bond to L$_n$, H, and C$_1$–C$_6$ alkyl;

R$^{20}$ and R$^{21}$ are independently selected from the group: H, C$_1$–C$_5$ alkyl, —CO$_2$R$^{25}$, C$_2$–C$_5$ 1-alkene substituted with 0–3 R$^{23}$, C$_2$–C$_5$ 1-alkyne substituted with 0–3 R$^{23}$, aryl substituted with 0–3 R$^{23}$, and unsaturated 5–10 membered heterocyclic ring system containing 1–4 heteroatoms independently selected from N, S, and O and substituted with 0–3 R$^{23}$;

alternatively, R$^{20}$ and R$^{21}$, taken together with the divalent carbon radical to which they are attached form:

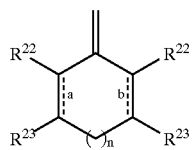

R$^{22}$ and R$^{23}$ are independently selected from the group: H, and R$^{24}$;

alternatively, R$^{22}$, R$^{23}$ taken together form a fused aromatic or a 5–10 membered heterocyclic ring system containing 1–4 heteroatoms independently selected from N, S, and O;

R$^{24}$ is independently selected at each occurrence from the group: —CO$_2$R$^{25}$, —C(=O)N(R$^{25}$)$_2$, —CH$_2$OR$^{25}$, —OC(=O)R$^{25}$, —OR$^{25}$, —SO$_3$H, —N(R$^{25}$)$_2$, and —OCH$_2$CO$_2$H; and, R$^{25}$ is independently selected at each occurrence from the group: hydrogen and C$_1$–C$_3$ alkyl.

[3] In an more preferred embodiment, the present invention provides a compound, wherein:

X$^1$ is threonine;

X$^2$ is lysine;

X$^5$ is arginine;

d is 1 or 2;

W is independently selected at each occurrence from the group: NHC(=O), C(=O)NH, and C(=O);

R$^6$, R$^{6a}$, R$^7$, R$^{7a}$, R$^8$, R$^{8a}$, R$^9$ and R$^{9a}$ are independently selected at each occurrence from the group: H benzyl substituted with 0–1 R$^{10}$, and a bond to C$_h$;

R$^{10}$ is OH;

h" is 0 or 1;

h''' is 0 or 1;

g is selected from 0, 1, 2, 3, 4, and 5;

g' is selected from 0, 1, 2, 3, 4, and 5;

g" is selected from 0, 1, 2, 3, 4, and 5;

g''' is selected from 0, 1, 2, 3, 4, and 5;

C$_h$ is a metal bonding unit having the formula:

R$^{13}$R$^{14}$N—NR$^{15}$R$^{16}$;

wherein:

R$^{13}$ is H;

R$^{14}$ is a heterocyclic ring system substituted with R$^{17}$, the heterocyclic ring system being selected from pyridine and pyrimidine;

R$^{17}$ is —C(=O)NHR$^{18}$;

R$^{18}$ is a bond to L$_n$;

R$^{24}$ is independently selected at each occurrence from the group: —CO$_2$R$^{25}$, —OR$^{25}$, —SO$_3$H, and —N(R$^{25}$)$_2$; and, R$^{25}$ is independently selected at each occurrence from the group: hydrogen and methyl.

[4] In another more preferred embodiment, the present invention provides a compound selected from the group consisting of:

6-((6-((1-aza-2-(2-sulfophenyl)vinyl)amino)-3-yridyl) carbonylamino)hexanoyl-L-threonyl-L-lysyl-L-prolyl-L-prolyl-L-arginine ((6-((1-aza-2-(2-sulfophenyl)vinyl)amino)-3-pyridyl) carbonyl)-L-phenylalanyl-6-aminohexanoyl-L-threonyl-L-lysyl-L-prolyl-L-prolyl-L-arginine ((6-((1-aza-2-(2-sulfophenyl)vinyl)amino)-3-pyridyl)
carbonyl)-L-tyrosinyl-6-aminohexanoyl-L-threonyl-L-
lysyl-L-prolyl-L-prolyl-L-arginine 6-((6-((1-aza-2-(2-sulfophenyl)vinyl)amino)-3-pyridyl)
carbonylamino)hexanoyl-L-threonyl-L-lysyl-L-
homoprolyl-L-prolyl-L-arginine 6-(hydrazino)-3-pyridylcarbonyl-glutamyl-(bis-(6-
aminohexanoyl-L-threonyl-L-lysyl-L-prolyl-L-prolyl-
L-arginine)).

[5] In another embodiment, the present invention provides a kit comprising a compound of the present invention.

[6] In another more preferred embodiment, the kit further comprises one or more ancillary ligands.

[7] In a still more preferred embodiment, the ancillary ligands are tricine and TPPTS.

[8] In another even more preferred embodiment, the kit further comprises a reducing agent.

[9] In a still more preferred embodiment, the kit further comprises one or more ancillary ligands.

[10] In a further preferred embodiment, the ancillary ligands are tricine and TPPTS.

[11] In another still more preferred embodiment, wherein the reducing agent is tin(II).

[12] In another further preferred embodiment, the kit further comprises one or more ancillary ligands.

[13] In an even further preferred embodiment, the ancillary ligands are tricine and TPPTS.

[14] In a second embodiment, the present invention provides a novel radiopharmaceutical comprising a complex of a compound of the present invention and a radioisotope selected from the group consisting of: $^{99m}$Tc, $^{186}$Re, and $^{188}$Re.

[15] In another more preferred embodiment, the radioisotope is $^{99m}$Tc.

[16] In still another more preferred embodiment, the radiopharmaceutical is selected from the group consisting of:

$^{99m}$Tc(tricine)(TPPTS)(6-((6-diazenido-3-pyridyl)
carbonylamino)hexanoyl-L-threonyl-L-lysyl-L-prolyl-
L-prolyl-L-arginine);

$^{99m}$Tc(tricine)(TPPTS)(((6-diazenido-3-pyridyl)
carbonyl)-L-phenylalanyl-6-aminohexanoyl-L-
threonyl-L-lysyl-L-prolyl-L-prolyl-L-arginine)

$^{99m}$Tc(tricine)(TPPTS)(((6-diazenido-3-pyridyl)
carbonyl)-L-tyrosinyl-6-aminohexanoyl-L-threonyl-L-
lysyl-L-prolyl-L-prolyl-L-arginine)

$^{99m}$Tc(tricine)(TPPTS)(6-((6-diazenido-3-pyridyl)
carbonylamino)hexanoyl-L-threonyl-L-lysyl-L-
homoprolyl-L-prolyl-L-arginine $^{99m}$Tc(tricine)(TPPTS)(6-(diazenido)-3-pyridylcarbonyl-
glutamyl-(bis-(6-aminohexanoyl-L-threonyl-L-lysyl-
L-prolyl-L-prolyl-L-arginine))).

[17] In another preferred embodiment, the radioisotope is is selected from the group consisting of: $^{186}$Re, and $^{188}$Re.

Another aspect of the present invention are diagnostic kits for the preparation of radiopharmaceuticals useful as imaging agents for infection, inflammation and cancer. Diagnostic kits of the present invention comprise one or more vials containing the sterile, non-pyrogenic, formulation comprised of a predetermined amount of a reagent of the present invention, and optionally other components such as one or two ancillary ligands, reducing agents, transfer ligands, buffers, lyophilization aids, stabilization aids, solubilization aids and bacteriostats. The inclusion of one or more optional components in the formulation will frequently improve the ease of synthesis of the radiopharmaceutical by the practicing end user, the ease of manufacturing the kit, the shelf-life of the kit, or the stability and shelf-life of the radiopharmaceutical. The inclusion of one or two ancillary ligands is required for diagnostic kits comprising reagent comprising a hydrazine or hydrazone bonding moiety. The one or more vials that contain all or part of the formulation can independently be in the form of a sterile solution or a lyophilized solid.

Another aspect of the present invention contemplates a method of imaging infection and inflammation in a patient involving: (1) synthesizing a diagnostic radiopharmaceutical of the present invention, using a reagent of the present invention, capable of localizing in infection and inflammation; (2) administering said radiopharmaceutical to a patient by injection or infusion; (3) imaging the patient using planar or SPECT gamma scintigraphy.

Another aspect of the present invention contemplates a method of imaging cancer in a patient involving: (1) synthesizing a diagnostic radiopharmaceutical of the present invention, using a reagent of the present invention, capable of localizing in tumors; (2) administering said radiopharmaceutical to a patient by injection or infusion; (3) imaging the patient using planar or SPECT gamma scintigraphy.

Another aspect of the present invention contemplates a method of treating cancer in a patient involving: (1) administering a therapeutic radiopharmaceutical of the present invention capable of localizing in tumors to a patient by injection or infusion.

DEFINITIONS

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention contain asymmetrically substituted carbon atoms, and may be isolated in optically active or racemic forms. It is well known in the art how to prepare optically active forms, such as by resolution of racemic forms or by synthesis from optically active starting materials. Two distinct isomers (cis and trans) of the peptide bond are known to occur; both can also be present in the compounds described herein, and all such stable isomers are contemplated in the present invention. The D and L-isomers of a particular amino acid are designated herein using the conventional 3-letter abbreviation of the amino acid, as indicated by the following examples: D-Leu, or L-Leu.

When any variable occurs more than one time in any substituent or in any formula, its definition on each occurrence is independent of its definition at every other occurrence. Thus, for example, if a group is shown to be substituted with 0–2 $R^{52}$, then said group may optionally be substituted with up to two $R^{52}$, and $R^{52}$ at each occurrence is selected independently from the defined list of possible $R^{52}$. Also, by way of example, for the group —N($R^{53}$)$_2$, each of the two $R^{53}$ substituents on N is independently selected from the defined list of possible $R^{53}$. Combinations of substituents and/or variables are permissible only if such combinations result in stable compounds. When a bond to a substituent is shown to cross the bond connecting two atoms in a ring, then such substituent may be bonded to any atom on the ring.

By "reagent" is meant a compound of this invention capable of direct transformation into a radiopharmaceutical of this invention. Reagents may be utilized directly for the preparation of the radiopharmaceuticals of this invention or may be a component in a kit of this invention.

The term "binding agent" means a radiopharmaceutical of this invention having affinity for and capable of binding to the tuftsin receptor. The binding agents of this invention have Ki<1000 nM.

By "stable compound" or "stable structure" is meant herein a compound that is sufficiently robust to survive isolation to a useful degree of purity from a reaction mixture, and formulation into an efficacious pharmaceutical agent.

The term "substituted", as used herein, means that one or more hydrogens on the designated atom or group is replaced with a selection from the indicated group, provided that the designated atom's or group's normal valency is not exceeded, and that the substitution results in a stable compound. When a substituent is keto (i.e., =O), then 2 hydrogens on the atom are replaced.

The term "bond", as used herein, means either a single or double bond.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as.carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

As used herein, "alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, hexyl, heptyl, octyl, nonyl, and decyl; "cycloalkyl" or "carbocycle" is intended to include saturated and partially unsaturated ring groups, including mono-, bi- or poly-cyclic ring systems, such as cyclopropyl, cyclobutyl, cyclopentyl, cyclohexyl, cycloheptyl, cyclooctyl and adamantyl; "bicycloalkyl" or "bicyclic" is intended to include saturated bicyclic ring groups such as [3.3.0]bicyclooctane, [4.3.0] bicyclononane, [4.4.0]bicyclodecane (decalin), [2.2.2] bicyclooctane, and so forth.

As used herein, the term "alkene" or "alkenyl" is intended to include hydrocarbon chains having the specified number of carbon atoms of either a straight or branched configuration and one or more unsaturated carbon-carbon bonds which may occur in any stable point along the chain, such as ethenyl, propenyl, and the like.

As used herein, the term "alkyne" or "alkynyl" is intended to include hydrocarbon chains having the specified number of carbon atoms of either a straight or branched configuration and one or more unsaturated carbon-carbon triple bonds which may occur in any stable point along the chain, such as propargyl, and the like.

As used herein, "aryl" or "aromatic residue" is intended to mean phenyl or naphthyl, which when substituted, the substitution can be at any position.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, uinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

A "reducing agent" is a compound that reacts with a radionuclide, which is typically obtained as a relatively unreactive, high oxidation state compound, to lower its oxidation state by transferring electron(s) to the radionuclide, thereby making it more reactive. Reducing agents useful in the preparation of radiopharmaceuticals and in diagnostic kits useful for the preparation of said radiopharmaceuticals include but are not limited to stannous chloride, stannous fluoride, formamidine sulfinic acid, ascorbic acid, cysteine, phosphines, and cuprous or ferrous salts. Other reducing agents are described in Brodack et. al., PCT Application 94/22496, which is incorporated herein by reference.

A "transfer ligand" is a ligand that forms an intermediate complex with a metal ion that is stable enough to prevent unwanted side-reactions but labile enough to be converted to a radiopharmaceutical. The formation of the intermediate complex is kinetically favored while the formation of the metallopharmaceutical is thermodynamically favored. Transfer ligands useful in the preparation of radiopharmaceuticals and in diagnostic kits useful for the preparation of diagnostic radiopharmaceuticals include but are not limited to gluconate, glucoheptonate, mannitol, glucarate, N,N,N',N'-ethylenediaminetetraacetic acid, pyrophosphate and methylenediphosphonate. In general, transfer ligands are comprised of oxygen or nitrogen donor atoms.

The term "donor atom" refers to the atom directly attached to a metal by a chemical bond.

"Ancillary" or "co-ligands" are ligands that are incorporated into a radiopharmaceutical during its synthesis. They serve to complete the coordination sphere of the radionuclide together with the chelator or radionuclide bonding unit of the reagent. For radiopharmaceuticals comprised of a binary ligand system, the radionuclide coordination sphere is composed of one or more chelators or bonding units from one or more reagents and one or more ancillary or co-ligands, provided that there are a total of two types of ligands, chelators or bonding units. For example, a radiopharmaceutical comprised of one chelator or bonding unit from one reagent and two of the same ancillary or co-ligands and a radiopharmaceutical comprised of two chelators or bonding units from one or two reagents and one ancillary or co-ligand are both considered to be comprised of binary ligand systems. For radiopharmaceuticals comprised of a ternary ligand system, the radionuclide coordination sphere is composed of one or more chelators or bonding units from one or more reagents and one or more of two different types of ancillary or co-ligands, provided that there are a total of three types of ligands, chelators or bonding units. For example, a radiopharmaceutical comprised of one chelator or bonding unit from one reagent and two different ancillary or co-ligands is considered to be comprised of a ternary ligand system.

Ancillary or co-ligands useful in the preparation of radiopharmaceuticals and in diagnostic kits useful for the preparation of said radiopharmaceuticals are comprised of one or more oxygen, nitrogen, carbon, sulfur, phosphorus, arsenic, selenium, and tellurium donor atoms. A ligand can be a transfer ligand in the synthesis of a radiopharmaceutical and also serve as an ancillary or co-ligand in another radiopharmaceutical. Whether a ligand is termed a transfer or ancillary or co-ligand depends on whether the ligand remains in the radionuclide coordination sphere in the radiopharmaceutical, which is determined by the coordination chemistry of the radionuclide and the chelator or bonding unit of the reagent or reagents.

A "chelator" or "bonding unit" is the moiety or group on a reagent that binds to a metal ion through the formation of chemical bonds with one or more donor atoms.

The term "binding site" means the site in vivo or in vitro that binds a biologically active molecule.

A "diagnostic kit" or "kit" comprises a collection of components, termed the formulation, in one or more vials which are used by the practicing end user in a clinical or pharmacy setting to synthesize diagnostic radiopharmaceuticals. The kit provides all the requisite components to synthesize and use the diagnostic radiopharmaceutical except those that are commonly available to the practicing end user, such as water or saline for injection, a solution of the radionuclide, equipment for heating the kit during the synthesis of the radiopharmaceutical, if required, equipment necessary for administering the radiopharmaceutical to the patient such as syringes and shielding, and imaging equipment.

Therapeutic radiopharmaceuticals are provided to the end user in their final form in a formulation contained typically in one vial, as either a lyophilized solid or an aqueous solution. The end user reconstitutes the lyophilized with water or saline and withdraws the patient dose or just withdraws the dose from the aqueous solution formulation as provided.

A "lyophilization aid" is a component that has favorable physical properties for lyophilization, such as the glass transition temperature, and is added to the formulation to improve the physical properties of the combination of all the components of the formulation for lyophilization.

A "stabilization aid" is a component that is added to the radiopharmaceutical or to the diagnostic kit either to stabilize the radiopharmaceutical or to prolong the shelf-life of the kit before it must be used. Stabilization aids can be antioxidants, reducing agents or radical scavengers and can provide improved stability by reacting preferentially with species that degrade other components or the radiopharmaceutical.

A "solubilization aid" is a component that improves the solubility of one or more other components in the medium required for the formulation.

A "bacteriostat" is a component that inhibits the growth of bacteria in a formulation either during its storage before use of after a diagnostic kit is used to synthesize a radiopharmaceutical.

The following abbreviations are used herein:

| | |
|---|---|
| Acm | acetamidomethyl |
| b-Ala, beta-Ala or bAla | 3-aminopropionic acid |
| ATA | 2-aminothiazole-5-acetic acid or 2-aminothiazole-5-acetyl group |

-continued

| | |
|---|---|
| Boc | t-butyloxycarbonyl |
| CBZ, Cbz or Z | Carbobenzyloxy |
| Dap | 2,3-diaminopropionic acid |
| DCC | dicyclohexylcarbodiimide |
| DIEA | diisopropylethylamine |
| DMAP | 4-dimethylaminopyridine |
| EOE | ethoxyethyl |
| HBTU | 2-(1H-Benzotriazol-1-yl)-1,1,3,3-tetramethyluronium hexafluorophosphate |
| OcHex | O-cyclohexyl |
| OBzl | O-benzyl |
| oSu | O-succinimidyl |
| TBTU | 2-(1H-Benzotriazol-1-yl)-1,1,3,3-tetramethyluronium tetrafluoroborate |
| THF | tetrahydrofuranyl |
| THP | tetrahydropyranyl |
| Tos | tosyl |
| Tr | trityl |

The following conventional three-letter amino acid abbreviations are used herein; the conventional one-letter amino acid abbreviations are NOT used herein:

| | | |
|---|---|---|
| Ala | = | alanine |
| Arg | = | arginine |
| Asn | = | asparagine |
| Asp | = | aspartic acid |
| Cys | = | cysteine |
| Gln | = | glutamine |
| Glu | = | glutamic acid |
| Gly | = | glycine |
| His | = | histidine |
| Ile | = | isoleucine |
| Leu | = | leucine |
| Lys | = | lysine |
| Met | = | methionine |
| Nle | = | norleucine |
| Orn | = | ornithine |
| Phe | = | phenylalanine |
| Phg | = | phenylglycine |
| Pro | = | proline |
| Sar | = | sarcosine |
| Ser | = | serine |
| Thr | = | threonine |
| Trp | = | tryptophan |
| Tyr | = | tyrosine |
| Val | = | valine |

The radiopharmaceuticals of the present invention are synthesized from the reagents of the present invention of formula, $C_h$—$L_n$—$(X^1X^2X^3X^4X^5)_d$, wherein d is 1–3 and $L_n$ represents an optional linking group, by reaction of said reagents with a Tc-99m-pertechnetate or Re-186 or Re-188-perrhenate ion. The peptides, $X^1X^2X^3X^4X^5$, are comprised of a pentapeptide sequence that binds to the tuftsin receptor which can be attached to $L_n$ or $C_h$. The interaction of the pentapeptide recognition sequences of radiopharmaceuticals with the tuftsin receptor results in localization of the radiopharmaceuticals on white cells which accumulate at the sites of infection and inflammation. It has also been found by the present inventors that these radiopharmaceuticals also localize in tumors.

The reagents of the present invention can be synthesized by several approaches. One approach involves the synthesis of the moiety, $X^1X^2X^3X^4X^5$, and direct attachment of one or more moieties, $X^1X^2X^3X^4X^5$, to the metal chelator or bonding moiety, $C_h$. Another approach involves the attachment of the one or more moieties, $X^1X^2X^3X^4X^5$, to the linking group, $L_n$, which is then attached to the group, $C_h$. Another approach involves the synthesis of the moiety, $L_n$—$X^1X^2X^3X^4X^5$, together, by incorporating an amino acid residue bearing $L_n$ into the synthesis of the peptide. The resulting moiety, $L_n$—$X^1X^2X^3X^4X^5$, is then attached to the moiety $C_h$. Another approach involves the synthesis of a peptide, $X^1X^2X^3X^4X^5$, bearing a fragment of the linking group, $L_n$, one or more of which are then attached to the remainder of the linking group and then to the moiety, $C_h$.

The peptides, $X^1X^2X^3X^4X^5$, optionally bearing a linking group, $L_n$, or a fragment of the linking group, can be synthesized using standard synthetic methods known to those skilled in the art. For example, one of skill in the art could use the synthetic procedures described in PCT Patent Application WO 94/22910, the contents of which are hereby incorporated by reference. Preferred methods include but are not limited to those methods described below.

Generally, peptides are elongated by deprotecting the alpha-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, or by solid phase peptide synthesis according to the method originally described by Merrifield, J. Am. Chem. Soc., 85, 2149–2154 (1963), the disclosure of which is hereby incorporated by reference. In addition to the foregoing, procedures for peptide synthesis are described in Stewart and Young, "Solid Phase Peptide Synthesis", 2nd ed, Pierce Chemical Co., Rockford, Ill. (1984); Gross, Meienhofer, Udenfriend, Eds., "The Peptides: Analysis, Synthesis, Biology, Vol. 1, 2, 3, 5, and 9, Academic Press, New York, (1980–1987); Bodanszky, "Peptide Chemistry: A Practical Textbook", Springer-Verlag, New York (1988); and Bodanszky et al. "The Practice of Peptide Synthesis" Springer-Verlag, New York (1984), the disclosures of which are hereby incorporated by reference.

The coupling between two amino acid derivatives, an amino acid and a peptide, two peptide fragments, or the cyclization of a peptide can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, Woodward reagent K method, carbonyldiimidazole method, phosphorus reagents such as BOP—Cl, or oxidation-reduction method. Some of these methods (especially the carbodiimide) can be enhanced by the addition of 1-hydroxybenzotriazole. These coupling reactions may be performed in either solution (liquid phase) or solid phase.

The functional groups of the constituent amino acids must be protected during the coupling reactions to avoid undesired bonds being formed. The protecting groups that can be used are listed in Greene, "Protective Groups in Organic Synthesis" John Wiley & Sons, New York (1981) and "The Peptides: Analysis, Synthesis, Biology, Vol. 3, Academic Press, New York (1981), the disclosure of which is hereby incorporated by reference.

The alpha-carboxyl group of the C-terminal residue is usually protected by an ester that can be cleaved to give the carboxylic acid. These protecting groups include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters. In the solid phase case, the C-terminal amino acid is attached to an insoluble carrier (usually polystyrene). These insoluble carriers contain a group which will react with the carboxyl group to form a bond which is stable to the elongation conditions but readily cleaved later. Examples of which are: oxime resin (DeGrado and Kaiser (1980) *J. Org. Chem.* 45, 1295–1300) chloro or bromomethyl resin, hydroxymethyl resin, and aminomethyl resin. Many of these resins are commercially available with the desired C-terminal amino acid already incorporated.

The alpha-amino group of each amino acid must be protected. Any protecting group known in the art can be used. Examples of these are: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. The preferred alpha-amino protecting group is either Boc or Fmoc. Many amino acid derivatives suitably protected for peptide synthesis are commercially available.

The alpha-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidines in dimethylformamide, but any secondary amine or aqueous basic solutions can be used. The deprotection is carried out at a temperature between 0° C. and room temperature.

Any of the amino acids bearing side chain functionalities must be protected during the preparation of the peptide using any of the above-identified groups. Those skilled in the art will appreciate that the selection and use of appropriate protecting groups for these side chain functionalities will depend upon the amino acid and presence of other protecting groups in the peptide. The selection of such a protecting group is important in that it must not be removed during the deprotection and coupling of the alpha-amino group.

For example, when Boc is chosen for the alpha-amine protection the following protecting groups are acceptable: p-toluenesulfonyl (tosyl) moieties and nitro for arginine; benzyloxycarbonyl, substituted benzyloxycarbonyls, tosyl or trifluoroacetyl for lysine; benzyl or alkyl esters such as cyclopentyl for glutamic and aspartic acids; benzyl ethers for serine and threonine; benzyl ethers, substituted benzyl ethers or 2-bromobenzyloxycarbonyl for tyrosine; p-methylbenzyl, p-methoxybenzyl, acetamidomethyl, benzyl, or t-butylsulfonyl for cysteine; and the indole of tryptophan can either be left unprotected or protected with a formyl group.

When Fmoc is chosen for the alpha-amine protection usually tert-butyl based protecting groups are acceptable. For instance, Boc can be used for lysine, tert-butyl ether for serine, threonine and tyrosine, and tert-butyl ester for glutamic and aspartic acids.

Once the elongation of the peptide is completed all of the protecting groups are removed. For the liquid phase synthesis the protecting groups are removed in whatever manner as dictated by the choice of protecting groups. These procedures are well known to those skilled in the art.

Unusual amino acids used in this invention can be synthesized by standard methods familiar to those skilled in the art ("The Peptides: Analysis, Synthesis, Biology, Vol. 5, pp. 342–449, Academic Press, New York (1981)). N-Alkyl amino acids can be prepared using procedures described in previously (Cheung et al., (1977) *Can. J. Chem.* 55, 906; Freidinger et al., (1982) *J. Org. Chem.* 48, 77 (1982)), which are incorporated herein by reference.

The attachment of linking groups, $L_n$, to the peptides, $X^1X^2X^3X^4X^5$; chelators or bonding units, $C_h$, to the peptides, $X^1X^2X^3X^4X^5$, or to the linking groups, $L_n$; and peptides bearing a fragment of the linking group to the remainder of the linking group, in combination forming the moiety, $L_n$—$X^1X^2X^3X^4X^5$, and then to the moiety $C_h$; can all be performed by standard techniques. These include, but are not limited to, amidation, esterification, alkylation, and the formation of ureas or thioureas. Procedures for performing these attachments can be found in Brinkley, M., *Bioconjugate Chemistry* 1992, 3(1), which is incorporated herein by reference.

The linking group $L_n$ can serve several roles. First it provides a spacing group between the chelator or bonding moiety, $C_h$, and the one or more of the peptides, $X^1X^2X^3X^4X^5$, so as to minimize the possibility that the moiety $C_h$ when bound to the radioisotope will interfere with the interaction of the pentapeptide recognition sequence of $X^1X^2X^3X^4X^5$ with the tuftsin receptor. The necessity of incorporating a linking group in a reagent is dependent on the identity of $X^1X^2X^3X^4X^5$ and $C_h$. If $C_h$ cannot be attached to $X^1X^2X^3X^4X^5$ without substantially diminishing its affinity for the receptor, then a linking group is used. A linking group also provides a means of independently attaching multiple peptides, $X^1X^2X^3X^4X^5$, to one group that is attached to $C_h$.

The linking group also provides a means of incorporating a pharmacokinetic modifier into the metallopharmaceuticals of the present invention. The pharmacokinetic modifier serves to direct the biodistribution of the portion of the injected metallopharmaceutical that does not become associated with the tumor vasculature. A wide variety of functional groups can serve as pharmacokinetic modifiers, including, but not limited to, carbohydrates, polyalkylene glycols, peptides or other polyamino acids, and cyclodextrins. The modifiers can be used to enhance or decrease hydrophilicity and to enhance or decrease the rate of blood-clearance. The modifiers can also be used to direct the route of elimination of the metallopharmaceuticals. Preferred pharmacokinetic modifiers are those that result in moderate to fast blood clearance and enhanced renal excretion.

The metal chelator or bonding moiety, $C_h$, is a hydrazine. The hydrazine may bear a protecting group which can be displaced either prior to using the reagent to synthesize a radiopharmaceutical or preferably in situ during the synthesis of the radiopharmaceutical. Exemplary protecting groups for hydrazine bonding units are hydrazones which can be aldehyde or ketone hydrazones having substituents selected from hydrogen, alkyl, aryl and heterocycle. Particularly preferred hydrazones are described in co-pending U.S. Ser. No. 08/476,296 the disclosure of which is herein incorporated by reference in its entirety.

The hydrazine bonding unit when bound to a metal radionuclide is termed a hydrazido, or diazenido group and serves as the point of attachment of the radionuclide to the remainder of the radiopharmaceutical. A diazenido group can be either terminal (only one atom of the group is bound to the radionuclide) or chelating. In order to have a chelating diazenido group at least one other atom of the group must also be bound to the radionuclide. The atoms bound to the metal are termed donor atoms.

The coordination sphere of metal ion includes all the ligands or groups bound to the metal. For a transition metal radionuclide to be stable it typically has a coordination number (number of donor atoms) comprised of an integer greater than or equal to 4 and less than or equal to 8; that is there are 4 to 8 atoms bound to the metal and it is said to have a complete coordination sphere. The requisite coordination number for a stable radionuclide complex is determined by the identity of the radionuclide, its oxidation state, and the type of donor atoms. If the chelator or bonding unit does not provide all of the atoms necessary to stabilize the metal radionuclide by completing its coordination sphere, the coordination sphere is completed by donor atoms from other ligands, termed ancillary or co-ligands, which can also be either terminal or chelating.

A large number of ligands can serve as ancillary or co-ligands, the choice of which is determined by a variety of considerations such as the ease of synthesis of the radiopharmaceutical, the chemical and physical properties of the ancillary ligand, the rate of formation, the yield, and the number of isomeric forms of the resulting radiopharmaceuticals, the ability to administer said ancillary or co-ligand to a patient without adverse physiological consequences to said patient, and the compatibility of the ligand in a lyophilized kit formulation. The charge and lipophilicity of the ancillary ligand will effect the charge and lipophilicity of the radiopharmaceuticals. For example, the use of 4,5-dihydroxy-1,3-benzene disulfonate results in radiopharmaceuticals with an additional two anionic groups because the sulfonate groups will be anionic under physiological conditions. The use of N-alkyl substituted 3,4-hydroxypyridinones results in radiopharmaceuticals with varying degrees of lipophilicity depending on the size of the alkyl substituents.

Preferred technetium radiopharmaceuticals of the present invention are comprised of a hydrazido or diazenido bonding unit and an ancillary ligand, $A_{L1}$, or a bonding unit and two types of ancillary $A_{L1}$ and $A_{L2}$. Ancillary ligands $A_{L1}$ are comprised of two or more hard donor atoms such as oxygen and amine nitrogen (sp$^3$ hybridized). The donor atoms occupy at least two of the sites in the coordination sphere of the radionuclide metal; the ancillary ligand $A_{L1}$ serves as one of the three ligands in the ternary ligand system. Examples of ancillary ligands $A_{L1}$ include but are not limited to dioxygen ligands and functionalized aminocarboxylates. A large number of such ligands are available from commercial sources.

Ancillary dioxygen ligands include ligands that coordinate to the metal ion through at least two oxygen donor atoms. Examples include but are not limited to: glucoheptonate, gluconate, 2-hydroxyisobutyrate, lactate, tartrate, mannitol, glucarate, maltol, Kojic acid, 2,2-bis (hydroxymethyl)propionic acid, 4,5-dihydroxy-1,3-benzene disulfbnate, or substituted or unsubstituted 1,2 or 3,4 hydroxypyridinones. (The names for the ligands in these examples refer to either the protonated or non-protonated forms of the ligands.)

Functionalized aminocarboxylates include ligands that have a combination of amine nitrogen and oxygen donor atoms. Examples include but are not limited to: iminodiacetic acid, 2,3-diaminopropionic acid, nitrilotriacetic acid, N,N'-ethylenediamine diacetic acid, N,N,N'-ethylenediamine triacetic acid, hydroxyethylethylenediamine triacetic acid, and N,N'-ethylenediamine bis-hydroxyphenylglycine. (The names for the ligands in these examples refer to either the protonated or non-protonated forms of the ligands.)

A series of functionalized aminocarboxylates are disclosed by Bridger et. al. in U.S. Pat. No. 5,350,837, herein incorporated by reference, that result in improved rates of formation of technetium labeled hydrazino modified proteins. We have determined that certain of these aminocarboxylates result in improved yields of the radiopharmaceuticals of the present invention. The preferred ancillary ligands $A_{L1}$ functionalized aminocarboxylates that are derivatives of glycine; the most preferred is tricine(tris (hydroxymethyl)methylglycine).

The most preferred technetium radiopharmaceuticals of the present invention are comprised of a hydrazido or diazenido bonding unit and two types of ancillary designated $A_{L1}$ and $A_{L2}$. The second type of ancillary ligands $A_{L2}$ are comprised of one or more soft donor atoms selected from the group: phosphine phosphorus, arsine arsenic, imine nitrogen (sp$^2$ hybridized), sulfur (sp$^2$ hybridized) and carbon (sp hybridized); atoms which have p-acid character. Ligands $A_{L2}$ can be monodentate, bidentate or tridentate, the denticity is defined by the number of donor atoms in the ligand. One of the two donor atoms in a bidentate ligand and one of the three donor atoms in a tridentate ligand must be a soft donor atom. We have disclosed in co-pending U.S. Ser. No. 08/415,908, and U.S. Ser. No. 60/013,360 and U.S. Ser. No. 08/646,886, the disclosures of which are herein incorporated by reference in their entirety, that radiopharmaceuticals comprised of one or more ancillary or co-ligands $A_{L2}$ are more stable compared to radiopharmaceuticals that are not comprised of one or more ancillary ligands, $A_{L2}$; that is, they have a minimal number of isomeric forms, the relative ratios of which do not change significantly with time, and that remain substantially intact upon dilution.

The ligands $A_{L2}$ that are comprised of phosphine or arsine donor atoms are trisubstituted phosphines, trisubstituted arsines, tetrasubstituted diphosphines and tetrasubstituted diarsines. The ligands $A_{L2}$ that are comprised of imine nitrogen are unsaturated or aromatic nitrogen-containing, 5 or 6-membered heterocycles. The ligands that are comprised of sulfur (sp$^2$ hybridized) donor atoms are thiocarbonyls, comprised of the moiety C=S. The ligands comprised of carbon (sp hybridized) donor atoms are isonitriles, comprised of the moiety CNR, where R is an organic radical. A large number of such ligands are available from commercial sources. Isonitriles can be synthesized as described in European Pat. No. 0107734 and in U.S. Pat. No. 4,988,827, herein incorporated by reference.

Preferred ancillary ligands $A_{L2}$ are trisubstituted phosphines and unsaturated or aromatic 5 or 6 membered heterocycles. The most preferred ancillary ligands $A_{L2}$ are trisubstituted phosphines and unsaturated 5 membered heterocycles.

The ancillary ligands $A_{L2}$ may be substituted with alkyl, aryl, alkoxy, heterocycle, aralkyl, alkaryl and arylalkaryl groups and may or may not bear functional groups comprised of heteroatoms such as oxygen, nitrogen, phosphorus or sulfur. Examples of such functional groups include but are not limited to: hydroxyl, carboxyl, carboxamide, nitro, ether, ketone, amino, ammonium, sulfonate, sulfonamide, phosphonate, and phosphonamide. The functional groups may be chosen to alter the lipophilicity and water solubility of the ligands which may affect the biological properties of the radiopharmaceuticals, such as altering the distribution into non-target tissues, cells or fluids, and the mechanism and rate of elimination from the body.

The technetium and rhenium radiopharmaceuticals of the present invention comprised of a hydrazido or diazenido bonding unit can be easily prepared by admixing a salt of a radionuclide, a reagent of the present invention, an ancillary ligand $A_{L1}$, an ancillary ligand $A_{L2}$, and a reducing agent, in an aqueous solution at temperatures from 0 to 100° C. The technetium and rhenium radiopharmaceuticals of the present invention comprised of a tetradentate chelator having two nitrogen and two sulfur atoms can be easily prepared by admixing a salt of a radionuclide, a reagent of the present invention, and a reducing agent, in an aqueous solution at temperatures from 0 to 100° C.

When the bonding unit in the reagent of the present invention is present as a hydrazone group, then it must first be converted to a hydrazine, which may or may not be protonated, prior to complexation with the metal radionuclide. The conversion of the hydrazone group to the hydrazine can occur either prior to reaction with the radionuclide, in which case the radionuclide and the ancillary or co-ligand or ligands are combined not with the reagent but with a hydrolyzed form of the reagent bearing the chelator or bonding unit, or in the presence of the radionuclide in which case the reagent itself is combined with the radionuclide and the ancillary or co-ligand or ligands. In the latter case, the pH of the reaction mixture must be neutral or acidic.

Alternatively, the radiopharmaceuticals of the present invention comprised of a hydrazido or diazenido bonding unit can be prepared by first admixing a salt of a radionuclide, an ancillary ligand $A_{L1}$, and a reducing agent in an aqueous solution at temperatures from 0 to 100° C. to form an intermediate radionuclide complex with the ancillary ligand $A_{L1}$ then adding a reagent of the present invention and an ancillary ligand $A_{L2}$ and reacting further at temperatures from 0 to 100° C.

Alternatively, the radiopharmaceuticals of the present invention comprised of a hydrazido or diazenido bonding unit can be prepared by first admixing a salt of a radionuclide, an ancillary ligand $A_{L1}$, a reagent of the present invention, and a reducing agent in an aqueous solution at temperatures from 0 to 100° C. to form an intermediate radionuclide complex, and then adding an ancillary ligand $AL_2$ and reacting further at temperatures from 0 to 100° C.

The technetium and rhenium radionuclides are preferably in the chemical form of pertechnetate or perrhenate and a pharmaceutically acceptable cation. The pertechnetate salt form is preferably sodium pertechnetate such as obtained from commercial Tc-99m generators. The amount of pertechnetate used to prepare the radiopharmaceuticals of the present invention can range from 0.1 mCi to 1 Ci, or more preferably from 1 to 200 mCi.

The amount of the reagent of the present invention used to prepare the technetium and rhenium radiopharmaceuticals of the present invention can range from 0.01 $\mu$g to 10 mg, or more preferably from 0.5 $\mu$g to 200 $\mu$g. The amount used will be dictated by the amounts of the other reactants and the identity of the radiopharmaceuticals of the present invention to be prepared.

The amounts of the ancillary ligands $A_{L1}$ used can range from 0.1 mg to 1 g, or more preferably from 1 mg to 100 mg.

The exact amount for a particular radiopharmaceutical is a function of identity of the radiopharmaceuticals of the present invention to be prepared, the procedure used and the amounts and identities of the other reactants. Too large an amount of $A_{L1}$ will result in the formation of by-products comprised of technetium labeled $A_{L1}$ without a biologically active molecule or by-products comprised of technetium labeled biologically active molecules with the ancillary ligand $A_{L1}$ but without the ancillary ligand $A_{L2}$. Too small an amount of $A_{L1}$ will result in other by-products such as technetium labeled biologically active molecules with the ancillary ligand $A_{L2}$ but without the ancillary ligand $A_{L1}$, or reduced hydrolyzed technetium, or technetium colloid.

The amounts of the ancillary ligands $A_{L2}$ used can range from 0.001 mg to 1 g, or more preferably from 0.01 mg to 10 mg. The exact amount for a particular radiopharmaceutical is a function of the identity of the radiopharmaceuticals of the present invention to be prepared, the procedure used and the amounts and identities of the other reactants. Too large an amount of $A_{L2}$ will result in the formation of by-products comprised of technetium labeled $A_{L2}$ without a biologically active molecule or by-products comprised of technetium labeled biologically active molecules with the ancillary ligand $A_{L2}$ but without the ancillary ligand $A_{L1}$. If the reagent bears one or more substituents that are comprised of a soft donor atom, as defined above, at least a ten-fold molar excess of the ancillary ligand $A_{L2}$ to the reagent of formula 2 is required to prevent the substituent from interfering with the coordination of the ancillary ligand $A_{L2}$ to the metal radionuclide.

Suitable reducing agents for the synthesis of the radiopharmaceuticals of the present invention include stannous salts, dithionite or bisulfite salts, borohydride salts, and formamidinesulfinic acid, wherein the salts are of any pharmaceutically acceptable form. The preferred reducing agent is a stannous salt. The amount of a reducing agent used can range from 0.001 mg to 10 mg, or more preferably from 0.005 mg to 1 mg.

The specific structure of a radiopharmaceutical of the present invention comprised of a hydrazido or diazenido bonding unit will depend on the identity of the reagent of the present invention used, the identity of any ancillary ligand $A_{L1}$, the identity of any ancillary ligand $A_{L2}$, and the identity of the radionuclide. Radiopharmaceuticals comprised of a hydrazido or diazenido bonding unit synthesized using concentrations of reagents of <100 $\mu$g/mL, will be comprised of one hydrazido or diazenido group. Those synthesized using >1 mg/mL concentrations will be comprised of two hydrazido or diazenido groups from two reagent molecules. For most applications, only a limited amount of the biologically active molecule can be injected and not result in undesired side-effects, such as chemical toxicity, interference with a biological process or an altered biodistribution of the radiopharmaceutical. Therefore, the radiopharmaceuticals which require higher concentrations of the reagents comprised in part of the biologically active molecule, will have to be diluted or purified after synthesis to avoid such side-effects.

The identities and amounts used of the ancillary ligands $A_{L1}$ and $A_{L2}$ will determine the values of the variables y and z. The values of y and z can independently be an integer from 1 to 2. In combination, the values of y and z will result in a technetium coordination sphere that is made up of at least five and no more than seven donor atoms. For monodentate ancillary ligands $A_{L2}$, z can be an integer from 1 to 2; for bidentate or tridentate ancillary ligands $A_{L2}$, z is 1. The preferred combination for monodentate ligands is y equal to 1 or 2 and z equal to 1. The preferred combination for bidentate or tridentate ligands is y equal to 1 and z equal to 1.

The total time of preparation will vary depending on the identity of the metal ion, the identities and amounts of the reactants and the procedure used for the preparation. The preparations may be complete, resulting in >80% yield of the radiopharmaceutical, in 1 minute or may require more time. If higher purity radiopharmaceuticals are needed or desired, the products can be purified by any of a number of techniques well known to those skilled in the art such as liquid chromatography, solid phase extraction, solvent extraction, dialysis or ultrafiltration.

Buffers useful in the preparation of radiopharmaceuticals and in diagnostic kits useful for the preparation of said radiopharmaceuticals include but are not limited to phosphate, citrate, sulfosalicylate, and acetate. A more complete list can be found in the United States Pharmacopeia.

Lyophilization aids useful in the preparation of diagnostic kits useful for the preparation of radiopharmaceuticals include but are not limited to mannitol, lactose, sorbitol, dextran, Ficoll, and polyvinylpyrrolidine(PVP).

Stabilization aids useful in the preparation of radiopharmaceuticals and in diagnostic kits useful for the preparation of radiopharmaceuticals include but are not limited to ascorbic acid, cysteine, monothioglycerol, sodium bisulfite, sodium metabisulfite, gentisic acid, and inositol.

Solubilization aids useful in the preparation of radiopharmaceuticals and in diagnostic kits useful for the preparation of radiopharmaceuticals include but are not limited to ethanol, glycerin, polyethylene glycol, propylene glycol, polyoxyethylene sorbitan monooleate, sorbitan monoloeate, polysorbates, poly(oxyethylene)poly(oxypropylene)poly(oxyethylene) block copolymers (Pluronics) and lecithin. Preferred solubilizing aids are polyethylene glycol, and Pluronics.

Bacteriostats useful in the preparation of radiopharmaceuticals and in diagnostic kits useful for the preparation of radiopharmaceuticals include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or co-ligand and so forth.

The diagnostic radiopharmaceuticals are administered by intravenous injection, usually in saline solution, at a dose of 1 to 100 mCi per 70 kg body weight, or preferably at a dose of 5 to 50 mCi. Imaging is performed using known procedures.

The therapeutic radiopharmaceuticals are administered by intravenous injection, usually in saline solution, at a dose of 0.1 to 100 mCi per 70 kg body weight, or preferably at a dose of 0.5 to 5 mCi per 70 kg body weight.

Other features of the invention will become apparent in the course of the following descriptions of exemplary embodiments which are given for illustration of the invention and are not intended to be limiting thereof.

EXAMPLES

All chemicals and solvents (reagent grade) were used as supplied from the vendors cited without further purification. Fmoc-amino acids and other starting amino acids may be obtained commercially from Bachem Inc., Bachem Biosciences Inc. (Philadelphia, Pa.), Advanced ChemTech (Louisville, Ky.), Peninsula Laboratories (Belmont, Calif.), or Sigma (St. Louis, Mo.). 2-(1H-Benzotriazol-1-yl)-1,1,3,3-tetramethyluronium hexafluorophosphate (HBTU) and TBTU were purchased from Advanced ChemTech. N-methylmorpholine (NMM), m-cresol, D-2-aminobutyric acid (Abu), trimethylacetylchloride, diisopropylethylamine (DIEA), 1,2,4-triazole, stannous chloride dihydrate, and tris(3-sulfonatophenyl)phosphine trisodium salt (TPPTS) were purchased from Aldrich Chemical Company. Bis(3-sulfonatophenyl)phenylphosphine disodium salt (TPPDS) was prepared by the published procedure (Kuntz, E., U.S. Pat. No. 4,248,802). (3-sulfonatophenyl)diphenylphosphine monosodium salt (TPPMS) was purchased from TCI America, Inc. Tricine was obtained from Research Organics, Inc. Technetium-99m-pertechnetate ($^{99m}TcO_4^{31}$) was obtained from a DuPont Pharma $^{99}Mo/^{99m}Tc$ Technelite® generator. Dimethylformamide (DMF), ethyl acetate, chloroform ($CHCl_3$), methanol (MeOH), pyridine and hydrochloric acid (HCl) were obtained from Baker. Acetonitrile, dichloromethane (DCM), acetic acid (HOAc), trifluoroacetic acid (TFA), ethyl ether, triethylamine, acetone, and magnesium sulfate were commercially obtained. Absolute ethanol was obtained from Quantum Chemical.

General Procedure for Solid Phase Peptide Synthesis

"Teabags" (5.0 cm×5.0 cm) were made from 0.75 µm mesh polypropylene filters, filled with 0.5 g of Fmoc-Arg (Pmc)-Wang Resin and placed in a polypropylene reactor. The deprotection, washing, and coupling reactions were carried out in the polypropylene reactor by agitation on a shaker table. The "teabags" were combined into one reactor for the deprotection steps, washings, and when coupling the same amino acid. Deprotection of the fmoc group was achieved via treatment of the teabags with the following (10 mL/bag): DMF (2×3 min.), 20% piperidine in DMF (1×3 min. pre-wash), 20% piperidine in DMF (1×30 min.), DCM (8×3 min.), and DMF (3×3 min.).

The next fmoc-amino acid was coupled using five equivalents of each of the following; fmoc-amino acid, HBTU, HOBT, and diisopropylethylamine (DIEA) in DMF (10 mL/bag). The coupling reactions were allowed to proceed overnight (~18 h). This was followed by washing with (10 mL/bag) DMF (3×3 min.) and DCM (8×3 min.). The coupling yield for each newly added amino acid was determined by testing one representative teabag using the picric acid assay. For the most part, the coupling yield was about 97%. Finally, after the last amino acid is coupled, 6-(N-boc-hydrazino)-nicotinic acid was coupled using the conditions described above. The bag was then dried under high vacuum.

Example 1

Synthesis of 6-((6-((1-aza-2-(2-Sulfophenyl)vinyl)amino)-3-pyridyl)carbonylamino)hexanoyl-L-threonyl-L-lysyl-L-prolyl-L-prolyl-L-arginine

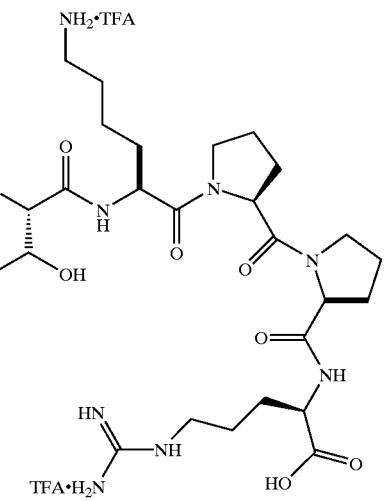

Part A: Preparation of 6-((6-Hydrazino-3-pyridyl)carbonylamino)-hexanoyl-L-threonyl-L-lysyl-L-prolyl-L-prolyl-L-arginine concentrated to an oil under high vacuum. The oil was triturated with ether to give 220 mg of crude product. A 50 mg portion of the crude product was purified Preparative HPLC Method 1 described below to give 20.9 mg of the purified product.

ESMS: Calcd. for $C_{38}H_{63}N_{13}O_9$, 845.49; Found, 844.3 [M–H]–1; Analytical HPLC, Method A, $R_t$=9.059 min., Purity 89%.

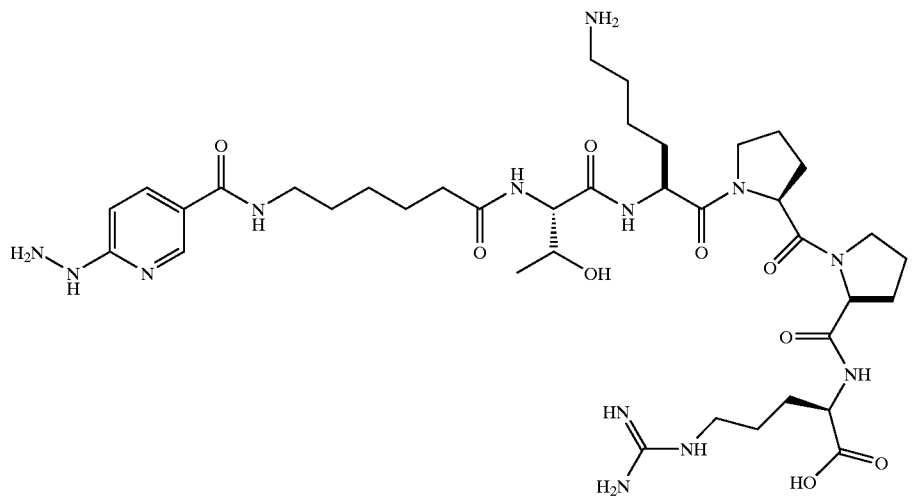

Contents of the "teabag" containing (6-(N-boc-hydrazino)-3-pyridylcarbonyl)-6-aminohexanoyl-Thr(OtBu)-Lys(boc)-Pro-Pro-Arg(Pmc)-Wang Resin were placed in a small erlenmeyer flask. To the flask was added 10 mL of a cleavage reagent comprising 95% trifluoroacetic acid (TFA), 2.5% triisopropylsilane, and 2.5% water. The resin was allowed to sit for two hours while occasionally being swirled. After each swirl the side of the flask was rinsed with additional cleavage reagent until the total volume of cocktail added was 15 mL. After two hours, the resin was filtered and washed with TFA (2×4 mL). The filtrate was Analytical HPLC, Method A Instrument: HP1050

Column: Vydac C18 (4.6×250 mm)

Detector: Diode array detector 220 nm/500 ref

Flow Rate: 1.0 mL/min.

Column Temp: 50° C.

Sample Size: 15 uL

Mobile Phase: A: 0.1% TFA in water
  B: 0.1% TFA in ACN/Water (9:1)

| Time (min) | % A | % B |
|---|---|---|
| 0 | 98 | 2 |
| 45 | 0 | 100 |
| 47 | 98 | 2 |

Preparative HPLC Method 1
Instrument: Rainin Rabbit; Dynamax software
Column: Vydac C-18 (21.2 mm×25 cm)
Detector: Knauer VWM
Flow Rate: 15 ml/min
Column Temp: RT
Mobile Phase: A: 0.05 M ammonium acetate
 B: 90% ACN 10% 0.05 M ammonium acetate

| Gradient: | Time (min) | % A | % B |
|---|---|---|---|
| | 0 | 98 | 2 |
| | 15 | 65 | 35 |
| | 16 | 0 | 100 |
| | 25 | 0 | 100 |
| | 27 | 98 | 2 |

Part B: Preparation of 6-((6-((1-Aza-2-(2-Sulfophenyl)vinyl)amino)-3-pyridyl)carbonylamino)hexanoyl-L-threonyl-L-lysyl-L-prolyl-L-prolyl-L-arginine 6-((6-Hydrazino-3-pyridyl)carbonylamino)-hexanoyl-L-threonyl-L-lysyl-L-prolyl-L-prolyl-L-arginine (0.100 g, 0.0842 mmol) was dissolved in dimethylformamide (2 mL). Triethylamine (35.2 µL, 0.253 mmol) was added, and the reaction was stirred for 5 min. 2-Formylbenzenesulfonic acid monosodium salt (0.0258 g, 0.0884 mmol) was dissolved in dimethylformamide (1 mL) and added dropwise to the reaction. The reaction mixture was stirred overnight for 18 h, then concentrated to an oil under high vacuum. The oil was triturated with ethyl acetate. The crude product was purified by Preparative HPLC Method 2 described below to give 9.7 mg (9%) of the desired product.

HRMS: Calcd. for $C_{45}H_{67}N_{13}O_{12}S+H$, 1014.4831; Found, 1014.4853. Analytical HPLC, Method A $R_t$=11.445 min., Purity=100%.

Preparative HPLC Method 2
Instrument: Rainin Rabbit; Dynamax software
Column: vydac C-18 (21.2 mm×25 cm)
Detector: Knauer VWM
Flow Rate: 15 ml/min
Column Temp: RT
Mobile Phase: A: 0.1% TFA in $H_2O$
 B: 0.1% TFA in ACN/$H_2O$ (9:1)

| Gradient: | Time (min) | % A | % B |
|---|---|---|---|
| | 0 | 85 | 15 |
| | 15 | 85 | 15 |
| | 16 | 80 | 20 |
| | 21 | 80 | 20 |
| | 22 | 0 | 100 |
| | 27 | 0 | 100 |
| | 28 | 85 | 15 |

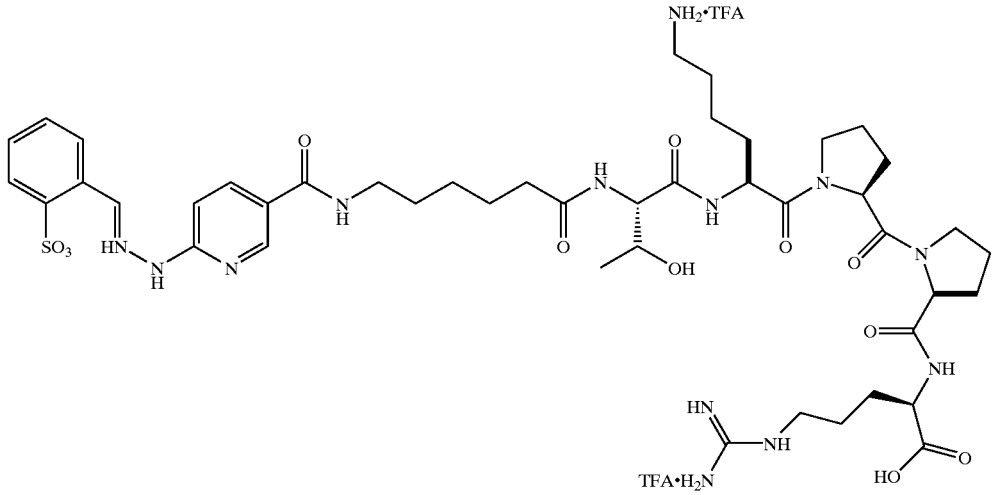

Example 2

Synthesis of ((6-((1-aza-2-(2-Sulfophenyl)vinyl) amino)-3-pyridyl)carbonyl)-L-phenylalanyl-6-aminohexanoyl-L-threonyl-L-lysyl-L-prolyl-L-prolyl-L-arginine

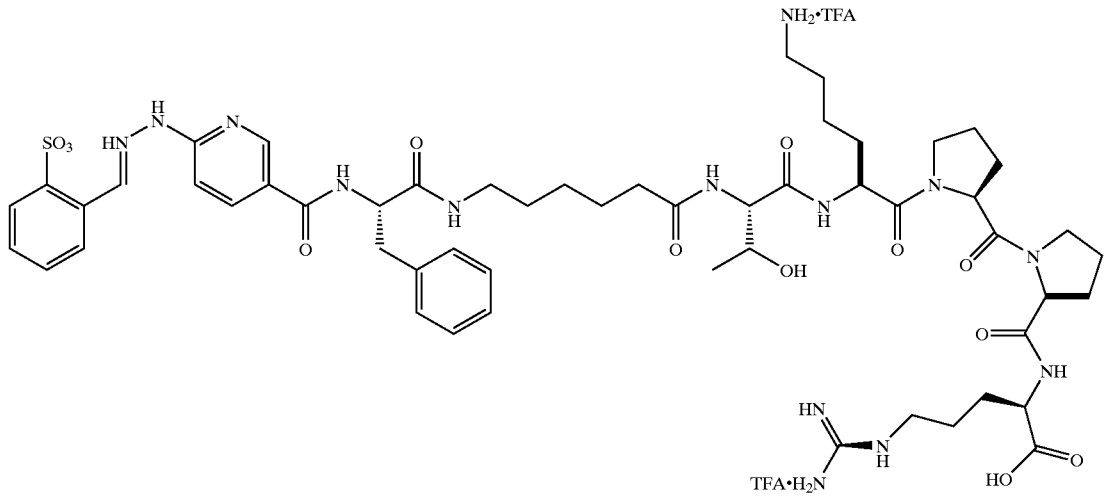

Part A: Preparation of ((6-Hydrazino-3-pyridyl)carbonyl)-L-phenylalanyl-6-aminohexanoyl-L-threonyl-L-lysyl-L-prolyl-L-prolyl-L-arginine

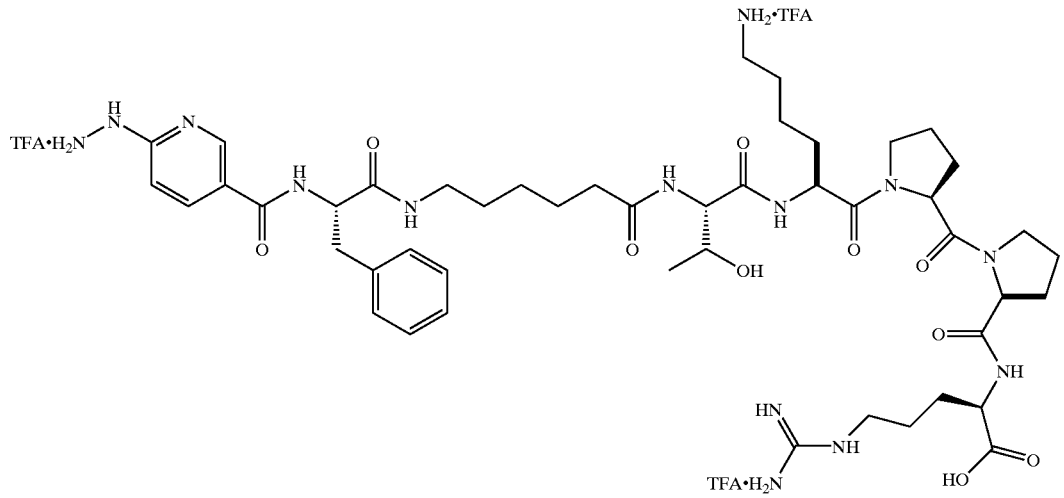

Contents of the ""teabag"" containing (6-(N-boc-hydrazino)-3-pyridylcarbonyl)-Phe-6-aminohexanoyl-Thr(OtBu)-Lys(boc)-Pro-Pro-Arg(Pmc)-Wang Resin were placed in a small erlenmeyer flask. To the flask was added 10 mL of a cleavage reagent comprising 95% trifluoroacetic acid (TFA), 2.5% triisopropylsilane, and 2.5% water. The resin was allowed to sit for two hours while occasionally being swirled. After each swirl the side of the flask was rinsed with additional cleavage reagent until the total volume of cocktail added was 15 mL. After two hours, the resin was filtered and washed with TFA (2×4 mL). The filtrate was concentrated to an oil under high vacuum. The oil was triturated with ether to give 222 mg of crude product.

ESMS: Calcd. for $C_{47}H_{72}N_{14}O_{10}$, 992.56; Found, 993.5 [M+H]+1; Analytical HPLC, Method A, $R_t$=12.443 min Purity=48%.

Part B: Preparation of ((6-((1-aza-2-(2-Sulfophenyl)vinyl) amino)-3-pyridyl)carbonyl)-L-phenylalanyl-6-aminohexanoyl-L-threonyl-L-lysyl-L-prolyl-L-prolyl-L-arginine ((6-Hydrazino-3-pyridyl)carbonyl)-L-phenylalanyl-6-aminohexanoyl-L-threonyl-L-lysyl-L-prolyl-L-prolyl-L-arginine (0.106 g, 0.0793 mmol) was dissolved in dimethylformamide (2 mL). Triethylamine (33.2 µL, 0.238 mmol) was added, and the reaction was stirred for 5 min. 2-Formylbenzenesulfonic acid monosodium salt (0.0173 g, 0.0833 mmol) was dissolved in dimethylformamide (1 mL) and added dropwise to the reaction. The reaction mixture was stirred overnight for 18 h, then concentrated to an oil under high vacuum. The oil was triturated with ethyl acetate. The crude product was purified by Preparative HPLC Method 2 to give 16.7 mg (15%) of the desired product.

HRMS: Calcd. for $C_{54}H_{76}N_{14}O_{13}S$+H, 1161.5515; Found, 1161.5520. Analytical HPLC, Method A $R_t$=14.735 min., Purity=86%.

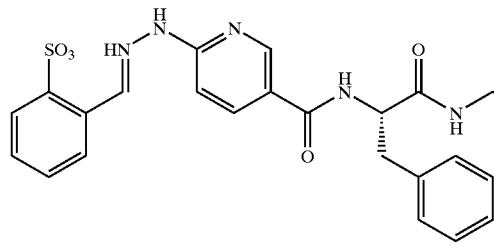
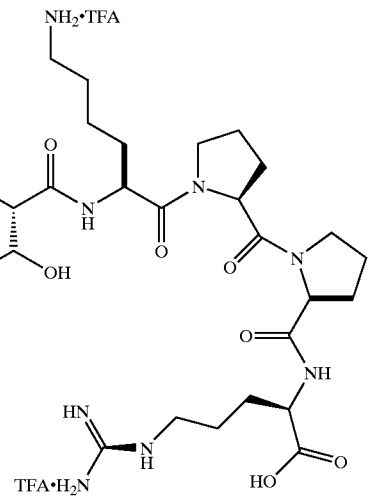

Example 3

Synthesis of ((6-((1-aza-2-(2-Sulfophenyl)vinyl) amino)-3-pyridyl)carbonyl)-L-tyrosinyl-6-aminohexanoyl-L-threonyl-L-lysyl-L-prolyl-L-prolyl-L-arginine

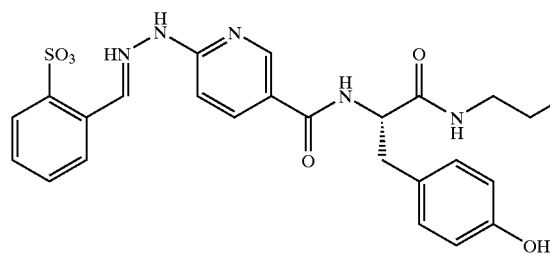
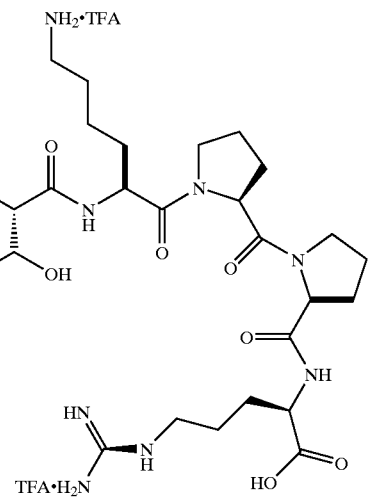

Part A: Preparation of ((6-Hydrazino-3-pyridyl)carbonyl)-L-tyrosinyl-6-aminohexanoyl-L-threonyl-L-lysyl-L-prolyl-L-prolyl-L-arginine

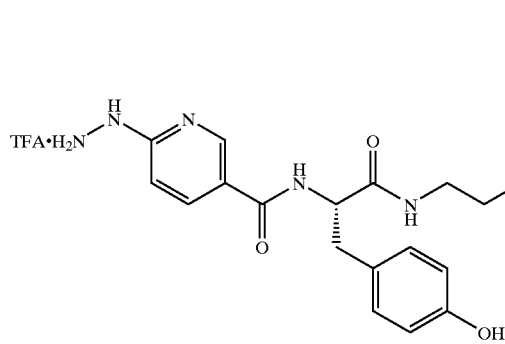

Contents of the ""teabag"" containing (6-(N-boc-hydrazino)-3-pyridylcarbonyl)-Tyr(OtBu)-6-aminohexanoyl-Thr(OtBu)-Lys(boc)-Pro-Pro-Arg(Pmc)-Wang Resin were placed in a small erlenmeyer flask. To the flask was added 10 mL of a cleavage reagent comprising 95% trifluoroacetic acid (TFA), 2.5% triisopropylsilane, and 2.5% water. The resin was allowed to sit for two hours while occasionally being swirled. After each swirl the side of the flask was rinsed with additional cocktail until the total volume of cocktail added was 15 mL. After two hours, the resin was filtered and washed with TFA (2×4 mL). The filtrate was concentrated to an oil under high vacuum. The oil was triturated with ether to give 235 mg of crude product.

ESMS: Calcd. for $C_{47}H_{72}N_{14}O_{11}$, 1008.55; Found, 1009.5 [M+H]+1; Analytical HPLC, Method A, $R_t$=10.513 min Purity=44%.

Part B: Preparation of ((6-((1-aza-2-(2-Sulfophenyl)vinyl)amino)-3-pyridyl)carbonyl)-L-tyrosinyl-6-aminohexanoyl-L-threonyl-L-lysyl-L-prolyl-L-prolyl-L-arginine ((6-Hydrazino-3-pyridyl)carbonyl)-L-tyrosinyl-6-aminohexanoyl-L-threonyl-L-lysyl-L-prolyl-L-prolyl-L-arginine (0.104 g, 0.0767 mmol) was dissolved in dimeth-

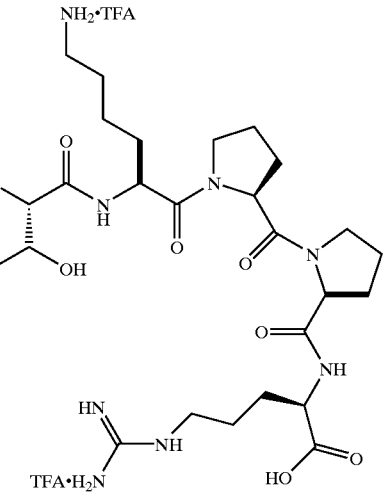

ylformamide (2 mL). Triethylamine (32.1 µL, 0.253 mmol) was added, and the reaction was stirred for 5 min. 2-Formylbenzenesulfonic acid monosodium salt (0.0258 g, 0.0805 mmol) was dissolved in dimethylformamide (1 mL) and added dropwise to the reaction. The reaction mixture was stirred overnight for 18 h, then concentrated to an oil under high vacuum. The oil was triturated with ethyl acetate. The crude product was purified by Preparative HPLC Method 1 to give 32.5 mg (30%) of the desired product.

HRMS: Calcd. for $C_{54}H_{76}N_{14}O_{14}S$+H, 1177.5464; Found, 1177.5496. Analytical HPLC, Method A $R_t$=12.564 min Purity=90%.

Example 4

Synthesis of 6-((6-((1-aza-2-(2-Sulfophenyl)vinyl)amino)-3-pyridyl)carbonylamino)hexanoyl-L-threonyl-L-lysyl-L-homoprolyl-L-prolyl-L-arginine

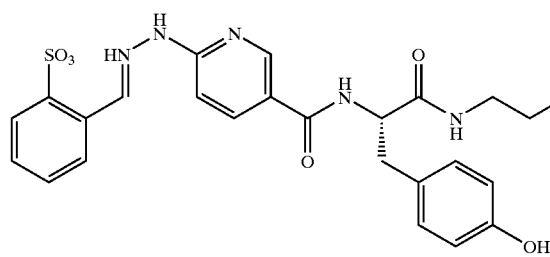

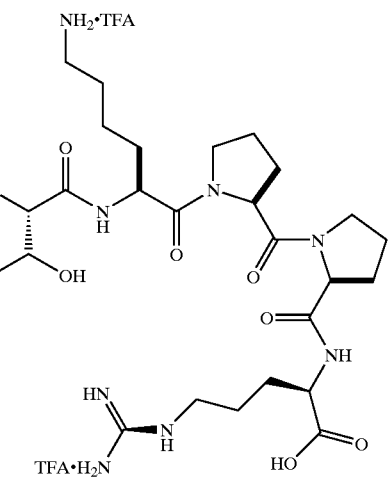

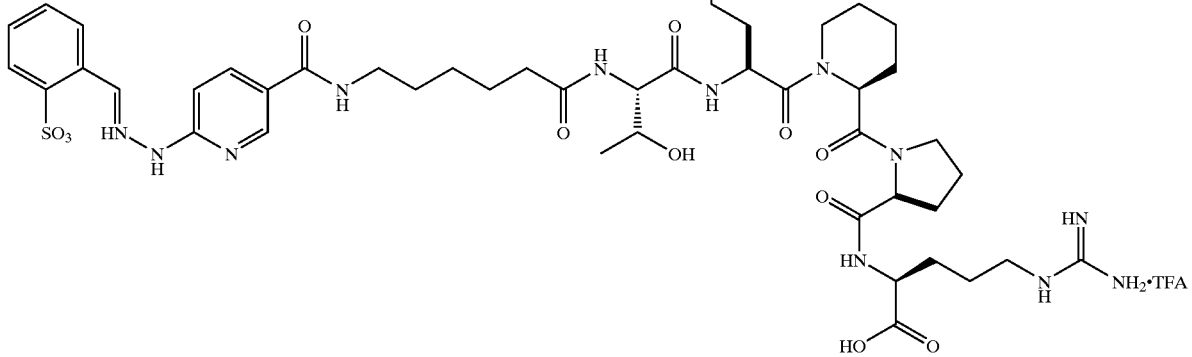

Part A: Preparation of 6-((6-Hydrazino-3-pyridyl)carbonylamino)-hexanoyl-L-threonyl-L-lysyl-L-homoprolyl-L-prolyl-L-arginine

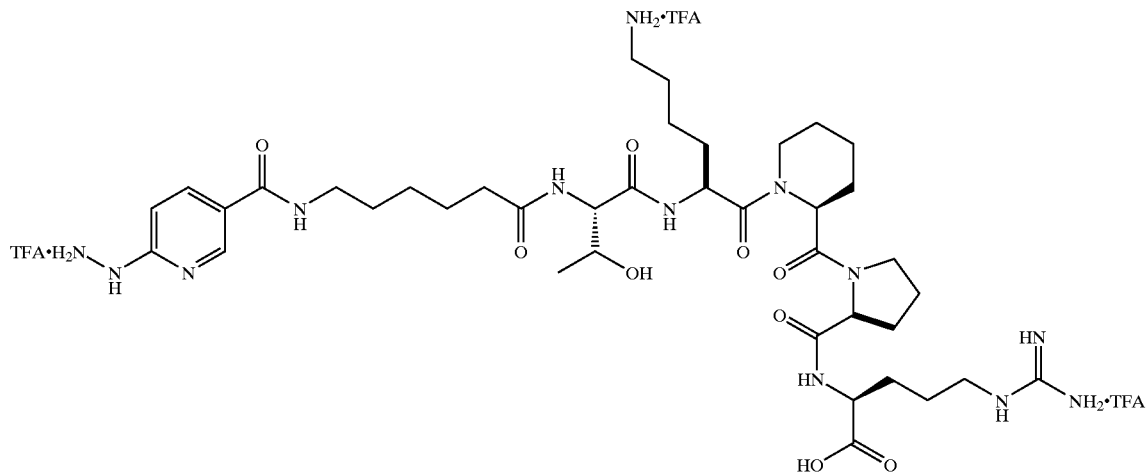

Contents of the ""teabag"" containing (6-(N-boc-hydrazino)-3-pyridylcarbonyl)-6-aminohexanoyl-Thr(OtBu)-Lys(boc)-HPro-Pro-Arg(Pmc)-Wang Resin were placed in a small erlenmeyer flask. To the flask was added 10 mL of a cleavage reagent comprising 95% trifluoroacetic acid (TEA), 2.5% triisopropylsilane, and 2.5% water. The resin was allowed to sit for two hours while occasionally being swirled. After each swirl the side of the flask was rinsed with additional cleavage reagent until the total volume of cocktail added was 15 mL. After two hours, the resin was filtered and washed with TFA (2×4 mL). The filtrate was concentrated to an oil under high vacuum. The oil was triturated with ether to give 0.128 g of crude product.

ESMS: Calcd. for $C_{39}H_{65}N_{13}O_9$, 859.50; Found, 860.5 [M+H]+1; Analytical HPLC, Method B, $R_t$=10.057 min Purity=13%.

Analytical HPLC Method B
Instrument: HP1050
Column: Vydac C18 (4.6×250 mm)
Detector: Diode array detector 220 nm/500 ref
Flow Rate: 1.0 mL/min.
Column Temp: 50° C.
Sample Size: 15 uL
Mobile Phase: A: 0.1% TFA in water
B: 0.1% TFA in ACN/Water (9:1)

| Time (min) | % A | % B |
|---|---|---|
| 0 | 98 | 2 |
| 16 | 63.2 | 36.8 |
| 18 | 0 | 100 |
| 28 | 0 | 100 |
| 30 | 98 | 2 |

Part B: Preparation of 6-((6-((1-aza-2-(2-Sulfophenyl)vinyl)amino)-3-pyridyl)carbonylamino)hexanoyl-L-threonyl-L-lysyl-L-homoprolyl-L-prolyl-L-arginine

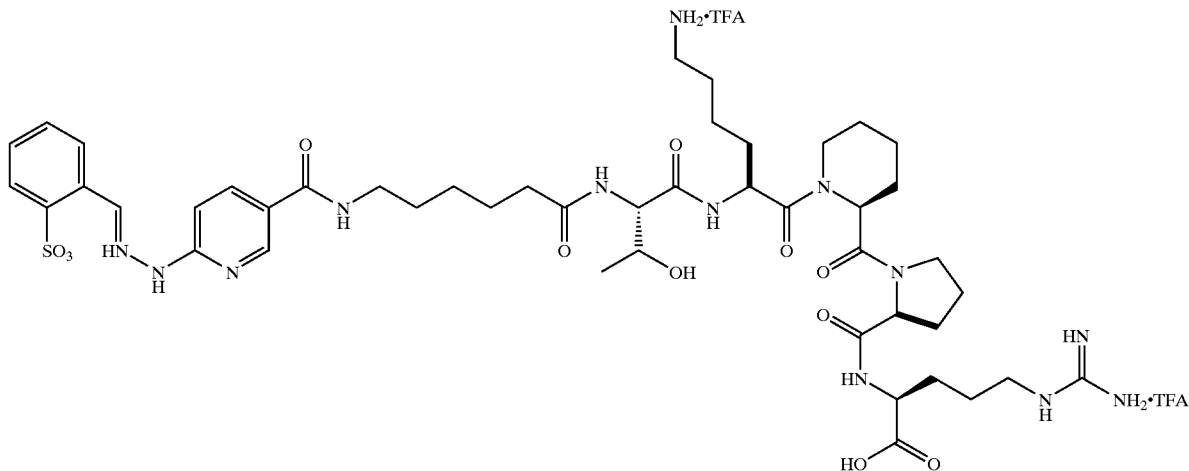

6-((6-Hydrazino-3-pyridyl)carbonylamino)-hexanoyl-L-threonyl-L-lysyl-L-homoprolyl-L-prolyl-L-arginine (0.100 g, 0.116 mmol) was dissolved in dimethylformamide (2 mL). Triethylamine (48.5 µL, 0.348 mmol) was added, and the reaction was stirred for 5 min. 2-Formylbenzenesulfonic acid monosodium salt (0.0254 g, 0.122 mmol) was dissolved in dimethylformamide (1 mL) and added dropwise to the reaction. The reaction mixture was stirred overnight for 18 h, then concentrated to an oil under high vacuum. The oil was triturated with ethyl acetate. The crude product was purified by Preparative HPLC Method 1 to give 9.7 mg (9%) of the desired product.

ESMS: Calcd. for $C_{46}H_{69}N_{13}O_{12}S$, 1027.49; Found, 1028.6.[M+H+1]; Analytical HPLC, Method B $R_t$=11.976 min Purity=100%.

Example 5

Synthesis of 6-(((tert-Butoxy)carbonylamino)-amino)-3-pyridylcarbonyl-glutamyl-(bis-(6-aminohexanoyl-L-threonyl-L-lysyl-L-prolyl-L-prolyl-L-arginine))penta TFA Salt

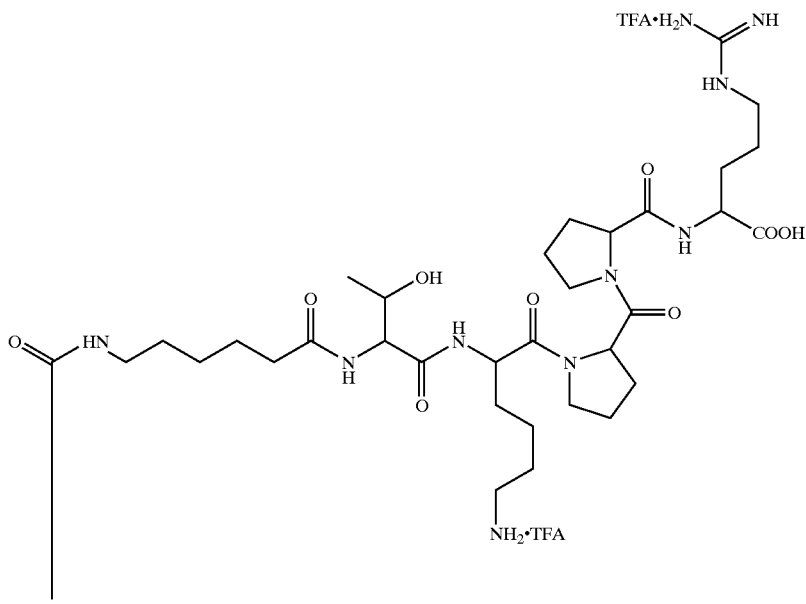

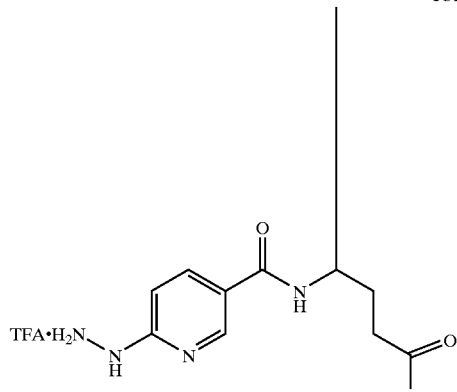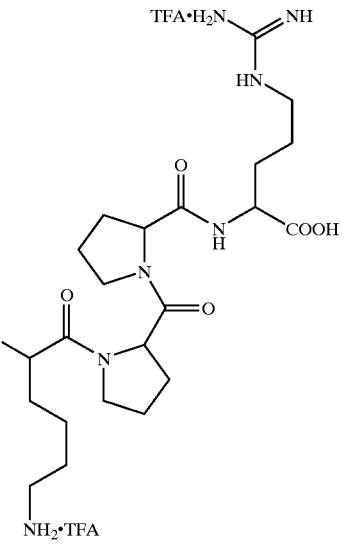

Part A: Preparation of Fmoc-6-Aminohexanoyl-L-threonyl-L-lysyl-L-prolyl-L-prolyl-L-arginine Contents of the "teabags" containing Fmoc-6-aminohexanoyl-Thr(OtBu)-Lys(boc)-Pro-Pro-Arg(Pmc)-Wang Resin (1.15 g) were placed in a small erlenmeyer flask. To the flask was added 10 mL of a cleavage reagent comprising 95% trifluoroacetic acid (TFA), 2.5% triisopropylsilane, and 2.5% water. The resin was allowed to sit for two hours while occasionally being swirled. After each swirl the side of the flask was rinsed with additional cleavage reagent until the total volume of cocktail added was 15 mL. After two hours, the resin was filtered and washed with TFA (2×4 mL). The filtrate was concentrated to an oil under high vacuum. The oil was triturated with ether to give 392.8 mg of crude product which was used directly in the following step.

ESMS: Calcd. for $C_{47}H_{68}N_{10}O_{10}$, 932.51; Found, 933.4 [M+H]+1; Analytical HPLC, Method A, $R_t$=11.56 min., Purity=91%.

Part B: Preparation of Fmoc-6-Aminohexanoyl-L-threonyl-L-lysyl(6-N-benzyloxycarbonyl)-L-prolyl-L-prolyl-L-arginine To a solution of Fmoc-6-aminohexanoyl-L-threonyl-L-lysyl-L-prolyl-L-prolyl-L-arginine (350 mg, 0.3 mmol) in DMF (5 mL) was added triethylamine (126 μL) and the reaction mixture stirred for 5 min.

Benzyloxycarbonyloxysuccinimide (90 mg, 0.3 mmol) was added, the solution stirred for 18 h at r.t under nitrogen and then concentrated to an oil in vacuo. The oil was triturated with ethyl acetate, the solid product filtered, washed with ethyl acetate and dried in vacuo to give 337.3 mg of the desired product which was used without further purification.

ESMS: Calcd. for $C_{55}H_{74}N_{10}O_{12}$, 1066.54; Found, 1067.8 [M+H]+1; Analytical HPLC, Method A, $R_t$=14.57 min., Purity=80%.

Part C: Preparation of 6-Aminohexanoyl-L-threonyl-L-lysyl(ε-N-benzyloxycarbonyl)-L-prolyl-L-prolyl-L-arginine. bis TFA Salt To a solution of Fmoc-6-aminohexanoyl-L-threonyl-L-lysyl(ε-N-benzyloxycarbonyl)-L-prolyl-L-prolyl-L-arginine (315 mg, 0.295 mmol) in DMF (8 mL) was added piperidine (2 mL) and the solution stirred under nitrogen for 2 h. The solution was concentrated to an oil in vacuo, triturated with ethyl acetate to give a solid which was filtered, washed with ethyl acetate and dried in vacuo and purified by preparative HPLC to give 103.6 mg (33%) of the product.

ESMS: Calcd. for $C_{40}H_{64}N_{10}O_{10}$, 844.5; Found, 845.4 [M+H]+1.

Part D: Preparation of N-boc-Glutamyl-(bis-(6-aminohexanoyl-L-threonyl-L-lysyl(ε-N-benzyloxycarbonyl)-L-prolyl-L-prolyl-L-arginine)). bis TFA Salt To a solution of 6-aminohexanoyl-L-threonyl-L-lysyl(ε-N-benzyloxycarbonyl)-L-prolyl-L-prolyl-L-arginine. bis TFA salt (121.9 mg, 0.114 mmol) in DMF (3 mL) was added triethyl amine (47.7 μL) and the reaction mixture was stirred for 5 min. To this was added boc-Glu(OSu)-OSu (25.3 mg), the reaction mixture stirred for 24 h under nitrogen, concentrated to an oil in vacuo and purified by preparative HPLC to give the desired product (63 mg, 36%).

ESMS: Calcd. for $C_{90}H_{141}N_{21}O_{24}$, 1900.0; Found, 1901.4 [M+H]+1.

Part E: Preparation of Glutamyl-(bis-(6-aminohexanoyl-L-threonyl-L-lysyl(ε-N-benzyloxycarbonyl)-L-prolyl-L-prolyl-L-arginine)). tris TFA Salt A solution of N-boc-glutamyl-(bis-(6-aminohexanoyl-L-threonyl-L-lysyl(ε-N-benzyloxycarbonyl)-L-prolyl-L-prolyl-L-arginine)). bis TFA salt in 50% TFA/DCM (2 mL) was stirred for 2 h, concentrated to an oil and triturated with diethyl ether to give the product, which was filtered, washed with diethyl ether and dried in vacuo (yield: 52.8 mg, 87%).

ESMS:Calcd. for $C_{85}H_{133}N_{21}O_{22}$, 1799.99; Found, 1801.3 [M+H]+1; Analytical HPLC, Method A, $R_t$=9.62 min., Purity=85%.

Part F: Preparation of 6-(((tert-Butoxy)carbonylamino) amino)-3-pyridylcarbonyl-glutamyl-(bis-(6-aminohexanoyl-L-threonyl-L-lysyl-L-prolyl-L-prolyl-L-arginine)). penta TFA Salt To a solution of glutamyl-(bis-(6-aminohexanoyl-L-threonyl-L-lysyl(ε-N-benzyloxycarbonyl)-L-prolyl-L-prolyl-L-arginine)). tris TFA salt (50 mg, 0.0233 mmol) in DMF (2 mL) was added triethylamine (9.7 μL) and the reaction mixture stirred for 5 min. 2,5-Dioxopyrrolidinyl 6-(((tert-butoxy)carbonylamino)-amino)pyridine-3-carboxylate (9.8 mg) was added, the reaction mixture stirred under nitrogen for 1 week and then concentrated to an oil in vacuo. The oil was purified by preparative HPLC to give the conjugated product (48 mg). Treatment with trifluoroacetic acid (1 mL) and triethylsilane (19.5 µL) gave the desired product (crude, 39 mg) upon trituration with ether.

ESMS:Calcd. for $C_{75}H_{126}N_{24}O_{19}$, 1666.96; Found, 834.7 [M+2H]+2.

Examples 6–10

The following examples describe the synthesis of radiopharmaceuticals of the present invention of the formula $^{99m}Tc(TfA)(tricine)(phosphine)$, in which (TfA) represents the tuftsin receptor antagonist compound bonded to the Tc through a diazenido (—N=N—) or hydrazido (=N—NH—) moiety. The diazenido or hydrazido moiety results from the reaction of the hydrazinonicotinamido group, present either as the free hydrazine or protected as a hydrazone, with the Tc-99m. The other two ligands in the Tc coordination sphere are tricine and a phosphine.

Synthesis of Tc-99m Tuftsin Receptor Antagonist Complexes of the Formula $^{99m}Tc(TfA)(tricine)$ (TPPTS)

To a lyophilized vial containing 4.84 mg TPPTS, 6.3 mg tricine, 40 mg mannitol, and 0.25 mmol succinate buffer, pH 4.8, was added 0.2–0.4 mL (20–40 µg) of a reagent of the present invention dissolved in saline or 50% aqueous ethanol, and 50–100 mCi $^{99m}TcO_4^-$ in saline, and additional saline to give a total volume of 1.3–1.5 mL. The kit is heated in an 100° C. water bath for 10–15 minutes, and is allowed to cool 10 minutes at room temperature. The sample is then analyzed by HPLC Method 1. If necessary, the complex was purified by injecting a 300–400 µL aliquot of the reaction mixture on the HPLC and collecting the product fraction. The fraction is then evaporated to dryness, redissolved in saline containing 0–5% by vol. Tween 80 and then re-analyzed by HPLC Method 1. Analytical and yield data for Examples 6–10 are shown in Table 1.

Analytical Methods

HPLC Method 1

Column: Zorbax C18, 25 cm×4.6 mm or Vydac C18, 25 cm×4.6 mm

Column Temperature: ambient

Flow: 1.0 mL/min

Solvent A: 10 mM sodium phosphate buffer pH 6

Solvent B: 100% Acetonitrile

Detector: sodium iodide (NaI) radiometric probe, UV 280 nm

| Gradient: | | | | | |
|---|---|---|---|---|---|
| t (min) | 0 | 20 | 30 | 31 | 40 |
| % B | 0 | 25 | 25 | 0 | 0 |

TABLE 1

Analytical and Yield Data for $^{99m}Tc$ Tuftsin Antagonist Complexes

| Complex Ex. No. | Reagent Ex. No. | % Yield | RT(min) |
|---|---|---|---|
| 6 | 1 | 92 | 11.1 |
| 7 | 2 | 94 | 15.5 |
| 8 | 3 | 86 | 13.4 |
| 9 | 4 | 87 | 10.9 |
| 10 | 5 | 80 | 12.8 |

Utility

The reagents of the present invention are useful for preparing radiopharmaceuticals of the present invention that bind to the tuftsin receptor on white blood cells. The radiopharmaceuticals of the present invention comprised of Tc-99m are useful for imaging of pathological processes involving the accumulation of white blood cells, including infection, inflammation and cancer. The radiopharmaceuticals of the present invention comprised of Re-186 or Re-188 are useful for treatment of pathological processes involving the accumulation of white blood cells, including infection, inflammation and cancer, by delivering a cytotoxic dose of radiation to the locus of white cell accumulation. The treatment of disease is affected by the systemic administration of the radiopharmaceuticals resulting in a cytotoxic radiation dose to tumors.

Representative compounds of the present invention were tested in the following in vitro and in vivo assays and models and were found to be active.

Guinea Pig Focal Infection Model

The function of the model is to rapidly assess an agent's ability to detect inflammation/infection as well as determine the biodistribution. Very briefly, the procedure was as follows: A #10 trochar needle was used to introduce a piece of umbilical tape immersed in a 6% sodium caseinate solution into the right flank and placed on the left side of the peritoneal cavity of anesthetized guinea pigs. The placement of the immersed string served as the focal site for white blood cell recruitment over the next eighteen hours. Eighteen hours later the guinea pigs were anesthetized and the test agent administered via the lateral saphenous vein. At the appropriate time postinjection, the animals were euthanized and the focal uptake determined. Throughout the course of the study blood was withdrawn via cardiac puncture. Uptake and target/background ratios were determined via well counting.

Rabbit Focal Infection Model

The function of the model is to rapidly assess an agent's ability to detect inflammation/infection via scintigraphy as well as determine the biodistribution. The protocol takes place over 2 days and is comprised of induction of an infection, imaging, followed by a biodistribution. Very briefly, the procedure was as follows: On day 1, $2\times10^9$ colonies of *E. coli* was administered intramuscularly in the thigh to anesthetized rabbits. The infection was permitted to fulminate for 24 hrs prior to the intravenous administration of the test agent. Prior to the administration of the test agent, the animal was anesthetized, intubated and monitored to assess arterial pressure and heart rate and hematology. Anterior 5 min serial images images were performed over a 4 hr period. At the end of the protocol the animal was euthanized with a pentobarbital overdose and the uptake of the test agent in various organs assessed via well counting.

Oncomouse® Imaging

The study involves the use of the c-Neu Oncomouse® and FVB mice simultaneously as controls. The mice are anesthetized with sodium pentobarbital and injected with approximately 0.5 mCi of radiopharmaceutical. Prior to injection, the tumor locations on each Oncomouse® are recorded and tumor size measured using calipers. The animals are positioned on the camera head so as to image the anterior or posterior of the animals. 5 Minute dynamic images are acquired serially over 2 hours using a 256×256 matrix and a zoom of 2×. Upon completion of the study, the images are evaluated by circumscribing the tumor as the target region of interest (ROI) and a background site in the neck area below the carotid salivary glands.

This model can also be used to assess the effectiveness of the radiopharmaceuticals of the present invention comprised of Re-186 or Re-188. The radiopharmaceuticals are administered in appropriate amounts and the uptake in the tumors can be quantified either non-invasively by imaging for these isotopes which have a coincident imageable gamma emission, or by excision of the tumors and counting the amount of radioactivity present by standard techniques. The therapeutic effect of the radiopharmaceuticals can be assessed by monitoring the rate of growth of the tumors in control mice versus those in the mice administered the radiopharmaceuticals of the present invention.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A compound having the formula:

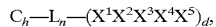

wherein:

$X^1$ is an amino acid independently selected from the group: threonine, serine, 3-hydroxyproline, and 4-hydroxyproline;

$X^2$ is an amino acid independently selected from the group: lysine, ornithine, arginine, 2-aminoethylcysteine, and glutamine;

$X^3$ and $X^4$ are amino acids independently selected at each occurrence from the group: proline, and homoproline;

$X^5$ is an amino acid independently selected from the group: lysine, ornithine, arginine, glutamine, and 2-amino-5-(2-imidazolin-2-ylamino)pentanoic acid;

d is selected from 1, 2, and 3;

$L_n$ is a linking group having the formula:

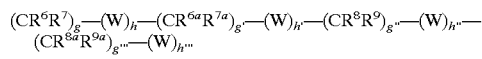

W is independently selected at each occurrence from the group: O, NH, NHC(=O), C(=O)NH, C(=O), C(=O)O, OC(=O);

$R^6$, $R^{6a}$, $R^7$, $R^{7a}$, $R^8$, $R^{8a}$, $R^9$ and $R^{9a}$ are independently selected at each occurrence from the group: =O, COOH, SO$_3$H, PO$_3$H, C$_1$–C$_5$ alkyl substituted with 0–3 $R^{10}$, aryl substituted with 0–3 $R^{10}$, benzyl substituted with 0–3 $R^{10}$, and C$_1$–C$_5$ alkoxy substituted with 0–3 $R^{10}$, NHC(=O)$R^{11}$, C(=O)NH$R^{11}$, NHC(=O)NH$R^{11}$, NH$R^{11}$, $R^{11}$, and a bond to $C_h$;

$R^{10}$ is independently selected at each occurrence from the group: a bond to $C_h$, COO$R^{11}$, OH, NH$R^{11}$, SO$_3$H, PO$_3$H, aryl substituted with 0–3 $R^{11}$, C$_{1-5}$ alkyl substituted with 0–1 $R^{12}$, C$_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, aryl substituted with 0–1 $R^{12}$, a 5–10 membered heterocyclic ring system containing 1–4 heteroatoms independently selected from N, S, and O and substituted with 0–1 $R^{12}$, C$_{3-10}$ cycloalkyl substituted with 0–1 $R^{12}$, and a bond to $C_h$;

$R^{12}$ is a bond to $C_h$;

h is selected from 0, 1, 2, 3, 4, and 5;

h' is selected from 0, 1, 2, 3, 4, and 5;

h" is selected from 0, 1, 2, 3, 4, and 5;

h'" is selected from 0, 1, 2, 3, 4, and 5;

g is selected from 0, 1, 2, 3, 4, 5, 6, 7, 8, 9, and 10;

g' is selected from 0, 1, 2, 3, 4, 5, 6, 7, 8, 9, and 10;

g" is selected from 0, 1, 2, 3, 4, 5, 6, 7, 8, 9, and 10;

g'" is selected from 0, 1, 2, 3, 4, 5, 6, 7, 8, 9, and 10;

$C_h$ is a metal bonding unit having the formula:

$$R^{13}R^{14}N-NR^{15}R^{16};$$

wherein:

$R^{13}$, and $R^{14}$ are each independently selected from the group: hydrogen, aryl substituted with 0–3 $R^{17}$, and a 5–10 membered heterocyclic ring system containing 1–4 heteroatoms independently selected from N, S, and O and substituted with 0–3 $R^{17}$;

$R^{15}$ and $R^{16}$ are both H, or combine to form =C($R^{20}$)($R^{21}$);

$R^{17}$ is independently selected at each occurrence from the group: a bond to $L_n$, F, Cl, Br, I, —CF$_3$, —CN, —CO$_2R^{18}$, —C(=O)$R^{18}$, —C(=O)N($R^{18}$)$_2$, —CH$_2$O$R^{18}$, —OC(=O)$R^{18}$, —OC(=O)O$R^{18}$, —O$R^{18}$, —SO$_2$N($R^{18}$)$_2$, C$_1$–C$_5$ alkyl, aryl substituted with 0–2 $R^{18}$, and a 5–10 membered heterocyclic ring system containing 1–4 heteroatoms independently selected from N, S, and O;

$R^{18}$ is independently selected at each occurrence from the group: a bond to $L_n$, H, C$_1$–C$_6$ alkyl, phenyl, and benzyl;

$R^{20}$ and $R^{21}$ are independently selected from the group: H, C$_1$–C$_{10}$ alkyl, —CN, —CO$_2R^{25}$, —C(=O)$R^{25}$, —C(=O)N($R^{25}$)$_2$, C$_2$–C$_{10}$ 1-alkene substituted with 0–3 $R^{23}$, C$_2$–C$_{10}$ 1-alkyne substituted with 0–3 $R^{23}$, aryl substituted with 0–3 $R^{23}$, unsaturated 5–10 membered heterocyclic ring system containing 1–4 heteroatoms independently selected from N, S, and O and substituted substituted with 0–3 $R^{23}$, and unsaturated C$_{3-10}$ carbocycle substituted with 0–3 $R^{23}$;

alternatively, $R^{20}$ and $R^{21}$, taken together with the divalent carbon radical to which they are attached form:

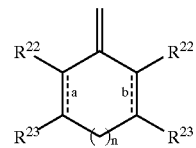

$R^{22}$ and $R^{23}$ are independently selected from the group: H, $R^{24}$, C$_1$–C$_{10}$ alkyl substituted with 0–3 $R^{24}$, C$_2$–C$_{10}$ alkenyl substituted with 0–3 $R^{24}$, C$_2$–C$_{10}$ alkynyl substituted with 0–3 $R^{24}$, aryl substituted with 0–3 $R^{24}$, a 5–10 membered heterocyclic ring system containing 1–4 heteroatoms independently selected from N, S, and O and substituted with 0–3 $R^{24}$, and C$_{3-10}$ carbocycle substituted with 0–3 $R^{24}$;

alternatively, $R^{22}$, $R^{23}$ taken together form a fused aromatic or a 5–10 membered heterocyclic ring system containing 1–4 heteroatoms independently selected from N, S, and O;

a and b indicate the positions of optional double bonds and n is 0 or 1;

$R^{24}$ is independently selected at each occurrence from the group: =O, F, Cl, Br, I, —CF$_3$, —CN, —CO$_2R^{25}$, —C(=O)$R^{25}$, —C(=O)N($R^{25}$)$_2$, —N($R^{25}$)$_3^+$, —CH$_2$O$R^{25}$, —OC(=O)$R^{25}$, —OC(=O)O$R^{25a}$, —O$R^{25}$, —OC(=O)N($R^{25}$)$_2$, —N$R^{26}$C(=O)$R^{25}$, —N$R^{26}$C(=O)O$R^{25a}$, —N$R^{26}$C(=O)N($R^{25}$)$_2$, —N$R^{26}$SO$_2$N($R^{25}$)$_2$, —N$R^{26}$SO$_2R^{25a}$, —SO$_3$H, —SO$_2R^{25a}$, —S$R^{25}$, —S(=O)$R^{25a}$, —SO$_2$N($R^{25}$)$_2$, —N($R^{25}$)$_2$, =NO$R^{25}$, —C(=O)NHO$R^{25}$, —OCH$_2$CO$_2$H, and 2-(1-morpholino)ethoxy; and, $R^{25}$, $R^{25a}$, and $R^{26}$ are each independently selected at each occurrence from the group: hydrogen and C$_1$–C$_6$ alkyl;

and a pharmaceutically acceptable salt thereof.

2. A compound of claim 1, wherein:

$X^1$ is an amino acid independently selected from the group: threonine, and serine;

$X^2$ is an amino acid independently selected from the group: lysine, and ornithine;

$X^5$ is an amino acid independently selected from the group: lysine, 2-amino-5-(2-imidazolin-2-ylamino) pentanoic acid, and arginine;

W is independently selected at each occurrence from the group: O, NH, NHC(=O), C(=O)NH, and C(=O);

$R^6$, $R^{6a}$, $R^7$, $R^{7a}$, $R^8$, $R^{8a}$, $R^9$ and $R^{9a}$ are independently selected at each occurrence from the group: =O, COOH, SO$_3$H, PO$_3$H, C$_1$–C$_5$ alkyl substituted with 0–1 $R^{10}$, aryl substituted with 0–1 $R^{10}$, benzyl substituted with 0–1 $R^{10}$, and C$_1$–C$_5$ alkoxy substituted with 0–1 $R^{10}$, NHC(=O)$R^{11}$, C(=O)NH$R^{11}$, NHC(=O)NH$R^{11}$, NH$R^{11}$, $R^{11}$, and a bond to $C_h$;

$R^{10}$ is independently selected at each occurrence from the group: a bond to $C_h$, COO$R^{11}$, OH, NH$R^{11}$, SO$_3$H, aryl substituted with 0–1 $R^{11}$, C$_{1-5}$ alkyl substituted with 0–1 $R^{12}$, C$_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, aryl substituted with 0–1 $R^{12}$, a 5–10 membered heterocyclic ring system containing 1–4 heteroatoms independently selected from N, S, and O and substituted with 0–1 $R^{12}$, and a bond to $C_h$;

h is 0 or 1;

h' is 0 or 1;

$C_h$ is a metal bonding unit having the formula:

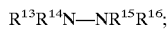

wherein:
$R^{17}$ is independently selected at each occurrence from the group: a bond to $L_n$, F, Cl, Br, I, —$CF_3$, —CN, —$CO_2R^{18}$, —C(=O)$R^{18}$, —C(=O)N($R^{18}$)$_2$, —$CH_2OR^{18}$, —OC(=O)$R^{18}$, —OC(=O)O$R^{18}$, —O$R^{18}$, and —$SO_2N(R^{18})_2$;

$R^{18}$ is independently selected at each occurrence from the group: a bond to $L_n$, H, and $C_1$–$C_6$ alkyl;

$R^{20}$ and $R^{21}$ are independently selected from the group: H, $C_1$–$C_5$ alkyl, —$CO_2R^{25}$, $C_2$–$C_5$ 1-alkene substituted with 0–3 $R^{23}$, $C_2$–$C_5$ 1-alkyne substituted with 0–3 $R^{23}$, aryl substituted with 0–3 $R^{23}$, and unsaturated 5–10 membered heterocyclic ring system containing 1–4 heteroatoms independently selected from N, S, and O and substituted with 0–3 $R^{23}$;

alternatively, $R^{20}$ and $R^{21}$, taken together with the divalent carbon radical to which they are attached form:

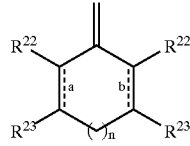

$R^{22}$ and $R^{23}$ are independently selected from the group: H, and $R^{24}$;

alternatively, $R^{22}$, $R^{23}$ taken together form a fused aromatic or a 5–10 membered heterocyclic ring system containing 1–4 heteroatoms independently selected from N, S, and O;

$R^{24}$ is independently selected at each occurrence from the group: —$CO_2R^{25}$, —C(=O)N($R^{25}$)$_2$, —$CH_2OR^{25}$, —OC(=O)$R^{25}$, —O$R^{25}$, —$SO_3H$, —N($R^{25}$)$_2$, and —$OCH_2CO_2H$; and, $R^{25}$ is independently selected at each occurrence from the group: hydrogen and $C_1$–$C_3$ alkyl.

3. A compound of claim 2, wherein:
$X^1$ is threonine;
$X^2$ is lysine;
$X^5$ is arginine;
d is 1 or 2;
W is independently selected at each occurrence from the group: NHC(=O), C(=O)NH, and C(=O);
$R^6$, $R^{6a}$, $R^7$, $R^{7a}$, $R^8$, $R^{8a}$, $R^9$ and $R^{9a}$ are independently selected at each occurrence from the group: H benzyl substituted with 0–1 $R^{10}$, and a bond to $C_h$;
$R^{10}$ is OH;
h" is 0 or 1;
h'" is 0 or 1;
g is selected from 0, 1, 2, 3, 4, and 5;
g' is selected from 0, 1, 2, 3, 4, and 5;
g" is selected from 0, 1, 2, 3, 4, and 5;
g'" is selected from 0, 1, 2, 3, 4, and 5;
$C_h$ is a metal bonding unit having the formula:

wherein:
$R^{13}$ is H;
$R^{14}$ is a heterocyclic ring system substituted with $R^{17}$, the heterocyclic ring system being selected from pyridine and pyrimidine;
$R^{17}$ is —C(=O)$NHR^{18}$;
$R^{18}$ is a bond to $L_n$;
$R^{24}$ is independently selected at each occurrence from the group: —$CO_2R^{25}$, —$OR^{25}$, —$SO_3H$, and —N($R^{25}$)$_2$; and,
$R^{25}$ is independently selected at each occurrence from the group: hydrogen and methyl.

4. A compound of claim 1 selected from the group consisting of:
6-((6-((1-aza-2-(2-sulfophenyl)vinyl)amino)-3-pyridyl)carbonylamino)hexanoyl-L-threonyl-L-lysyl-L-prolyl-L-prolyl-L-arginine ((6-((1-aza-2-(2-sulfophenyl)vinyl)amino)-3-pyridyl)carbonyl)-L-phenylalanyl-6-aminohexanoyl-L-threonyl-L-lysyl-L-prolyl-L-prolyl-L-arginine ((6-((1-aza-2-(2-sulfophenyl)vinyl)amino)-3-pyridyl)carbonyl)-L-tyrosinyl-6-aminohexanoyl-L-threonyl-L-lysyl-L-prolyl-L-prolyl-L-arginine 6-((6-((1-aza-2-(2-sulfophenyl)vinyl)amino)-3-pyridyl)carbonylamino)hexanoyl-L-threonyl-L-lysyl-L-homoprolyl-L-prolyl-L-arginine 6-(hydrazino)-3-pyridylcarbonyl-glutamyl-(bis-(6-aminohexanoyl-L-threonyl-L-lysyl-L-prolyl-L-prolyl-L-arginine)).

5. A kit comprising a compound of claim 3.

6. A kit of claim 5 further comprising one or more ancillary ligands.

7. A kit of claim 6 wherein the ancillary ligands are tricine and TPPTS.

8. A kit of claim 5 further comprising a reducing agent.

9. A kit of claim 8 further comprising one or more ancillary ligands.

10. A kit of claim 9 wherein the ancillary ligands are tricine and TPPTS.

11. A kit of claim 8 wherein the reducing agent is tin(II).

12. A kit of claim 11 further comprising one or more ancillary ligands.

13. A kit of claim 12 wherein the ancillary ligands are tricine and TPPTS.

14. A radiopharmaceutical comprising a complex of a compound of claim 3, one or more ancillary ligands and a radioisotope selected from the group consisting of: $^{99m}$Tc, $^{186}$Re, and $^{188}$Re.

15. A radiopharmaceutical of claim 14, wherein the radioisotope is $^{99m}$Tc.

16. A radiopharmaceutical of claim 15 selected from the group consisting of:
$^{99m}$Tc(tricine)(TPPTS)(6-((6-diazenido-3-pyridyl)carbonylamino)hexanoyl-L-threonyl-L-lysyl-L-prolyl-L-prolyl-L-arginine);

$^{99m}$Tc(tricine)(TPPTS)(((6-diazenido-3-pyridyl)carbonyl)-L-phenylalanyl-6-aminohexanoyl-L-threonyl-L-lysyl-L-prolyl-L-prolyl-L-arginine)

$^{99m}$Tc(tricine)(TPPTS)(((6-diazenido-3-pyridyl)carbonyl)-L-tyrosinyl-6-aminohexanoyl-L-threonyl-L-lysyl-L-prolyl-L-prolyl-L-arginine)

$^{99m}$Tc(tricine)(TPPTS)(6-((6-diazenido-3-pyridyl)carbonylamino)hexanoyl-L-threonyl-L-lysyl-L-homoprolyl-L-prolyl-L-arginine $^{99m}$Tc(tricine)(TPPTS)(6-(diazenido)-3-pyridylcarbonyl-glutamyl-(bis-(6-aminohexanoyl-L-threonyl-L-lysyl-L-prolyl-L-prolyl-L-arginine))).

17. A radiopharmaceutical of claim 14, wherein the radioisotope is selected from the group consisting of: $^{186}$Re, and $^{188}$Re.

18. A method of detecting sites of infection and inflammation in a mammal comprising administering to said mammal a radiopharmaceutical of claim 15 and then detecting said sites using a radiation detecting probe.

19. A method of imaging sites of infection and inflammation in a mammal comprising administering to said mammal a radiopharmaceutical of claim 15 and then imaging said sites using a planar or ring gamma camera.

20. A method of detecting tumors in a mammal comprising administering to the mammal a radiopharmaceutical of claim 15 and then detecting the tumors using a radiation detecting probe.

21. A method of imaging tumors in a mammal comprising administering to the mammal a radiopharmaceutical of claim 15 and then imaging the tumors using a gamma camera.

22. A method of treating cancer in a mammal comprising imaging the mammal using administering a therapeutically effective amount of a radiopharmaceutical of claim 17.

* * * * *